US012731009B2

(12) United States Patent
Nishimura et al.

(10) Patent No.: US 12,731,009 B2
(45) Date of Patent: Sep. 8, 2026

(54) NON-TRANSITORY COMPUTER READABLE MEDIUM, INFORMATION PROCESSING DEVICE, INFORMATION PROCESSING METHOD, AND METHOD FOR GENERATING LEARNING MODEL

(71) Applicant: Xcoo, Inc., Tokyo (JP)

(72) Inventors: Kunihiro Nishimura, Tokyo (JP); Takashi Aoki, Tokyo (JP); Toshiki Takeuchi, Tokyo (JP); Jun Imura, Tokyo (JP)

(73) Assignee: Xcoo, Inc., Tokyo (JP)

( * ) Notice: Subject to any disclaimer, the term of this patent is extended or adjusted under 35 U.S.C. 154(b) by 872 days.

(21) Appl. No.: 18/017,766

(22) PCT Filed: Jul. 28, 2020

(86) PCT No.: PCT/JP2020/028900
§ 371 (c)(1),
(2) Date: Jan. 24, 2023

(87) PCT Pub. No.: WO2022/024221
PCT Pub. Date: Feb. 3, 2022

(65) Prior Publication Data
US 2023/0289569 A1 Sep. 14, 2023

(51) Int. Cl.
*G06N 3/0464* (2023.01)
*G06N 3/084* (2023.01)
*G16H 15/00* (2018.01)

(52) U.S. Cl.
CPC ........... *G06N 3/0464* (2023.01); *G06N 3/084* (2013.01); *G16H 15/00* (2018.01)

(58) Field of Classification Search
CPC ...... G06N 3/0464; G06N 3/084; G16H 50/20; G16H 50/70; G16H 15/00; G16H 10/40; G16H 20/10; G16B 40/20
See application file for complete search history.

(56) References Cited

U.S. PATENT DOCUMENTS

2007/0083396 A1 4/2007 Kanada et al.
2007/0220488 A1 9/2007 Wheadon et al.
(Continued)

FOREIGN PATENT DOCUMENTS

JP 2007-122679 A 5/2007
JP 2010-224645 A 10/2010
(Continued)

OTHER PUBLICATIONS

Kureshi, Nelofar, Syed Sibte Raza Abidi, and Christian Blouin. "A predictive model for personalized therapeutic interventions in non-small cell lung cancer." IEEE journal of biomedical and health informatics 20.1 (2014): 424-431. (Year: 2014).*
(Continued)

*Primary Examiner* — Randall K. Baldwin
(74) *Attorney, Agent, or Firm* — Christian S. Hans; Bret E. Field; Bozicevic, Field & Francis LLP

(57) ABSTRACT

The present disclosure provides, for example, a non-transitory computer readable medium including program instructions that automatically extracts a clinically important mutation from genome data.
The non-transitory computer readable medium including program instructions which when executed by a processor (21) causing a computer to execute a process comprising: acquiring, by the processor, training data in which genome data obtained by reading a base sequence included in a specimen and a genetic mutation according to the specimen are recorded in association with each other, for a plurality of genetic tests performed in the past; and generating, by the processor, a learning model (53) for outputting a prediction relevant to the genetic mutation based on the specimen in a case where the genome data obtained by reading the base sequence included in the specimen is input by setting the genome data as input and the genetic mutation as output.

20 Claims, 30 Drawing Sheets

(56) References Cited

U.S. PATENT DOCUMENTS

| | | | | |
|---|---|---|---|---|
| 2014/0011861 | A1 | 1/2014 | McClelland et al. | |
| 2014/0032125 | A1 | 1/2014 | Hawkins | |
| 2014/0177930 | A1 | 6/2014 | Osborne et al. | |
| 2014/0278133 | A1 | 9/2014 | Chen et al. | |
| 2016/0371431 | A1 | 12/2016 | Haque et al. | |
| 2017/0177790 | A1 | 6/2017 | Carmeli et al. | |
| 2017/0372003 | A1 | 12/2017 | Nishimura et al. | |
| 2018/0004905 | A1 | 1/2018 | Szeto | |
| 2018/0032673 | A1 | 2/2018 | Kinoshita et al. | |
| 2018/0247010 | A1 | 8/2018 | Razi et al. | |
| 2019/0018930 | A1 | 1/2019 | Kishi et al. | |
| 2019/0019085 | A1 | 1/2019 | Glode et al. | |
| 2020/0005893 | A1* | 1/2020 | Huettner | G16H 50/20 |
| 2020/0063202 | A1* | 2/2020 | Albertsen | C12Q 1/6869 |
| 2021/0090694 | A1* | 3/2021 | Colley | G16H 50/50 |
| 2023/0290439 | A1* | 9/2023 | Li | G06N 3/09 |

FOREIGN PATENT DOCUMENTS

| | | | |
|---|---|---|---|
| JP | 2016-516237 | A | 6/2016 |
| JP | 2016-154042 | A | 8/2016 |
| JP | 2018-513461 | A | 5/2018 |
| JP | 2018-527647 | A | 9/2018 |
| JP | 2018-532214 | A | 11/2018 |
| JP | 2019-020838 | A | 2/2019 |
| JP | 2020-144658 | A | 9/2020 |
| JP | 2020-144940 | A | 9/2020 |
| WO | WO2016035168 | A1 | 3/2016 |
| WO | WO2016175330 | A1 | 11/2016 |

OTHER PUBLICATIONS

Adetiba, Emmanuel, and Oludayo O. Olugbara. "Lung cancer prediction using neural network ensemble with histogram of oriented gradient genomic features." The Scientific World Journal 2015.1 (2015): 786013. (Year: 2015).*

Chen, Yukun, et al. "Classification of cancer primary sites using machine learning and somatic mutations." BioMed research international 2015.1 (2015): 491502. (Year: 2015).*

Adetiba, Emmanuel, and Oludayo O. Olugbara. "Improved classification of lung cancer using radial basis function neural network with affine transforms of voss representation." PloS one 10.12 (2015): e0143542. (Year: 2015).*

Krempel, Rasmus, et al. "Integrative analysis and machine learning on cancer genomics data using the Cancer Systems Biology Database (CancerSysDB)." BMC bioinformatics 19.1 (2018): 156. (Year: 2018).*

Wood, Derrick E., et al. "A machine learning approach for somatic mutation discovery." Science translational medicine 10.457 (2018): eaar7939. (Year: 2018).*

Shen, Jie, et al. "Identification of a novel gene signature for the prediction of recurrence in HCC patients by machine learning of genome-wide databases." Scientific reports 10.1 (Mar. 2020): 4435. (Year: 2020).*

Wu, Chao, et al. "Using machine learning to identify true somatic variants from next-generation sequencing." Clinical chemistry 66.1 (Jan. 2020): 239-246. (Year: 2020).*

Chiu, Yu-Chiao, et al. "Predicting drug response of tumors from integrated genomic profiles by deep neural networks." BMC medical genomics 12.Suppl 1 (2019): 18. (Year: 2019).*

English Translation of International Search Report for PCT Application No. PCT/JP2020/028900 mailed Oct. 27, 2020, 5 pages.

* cited by examiner

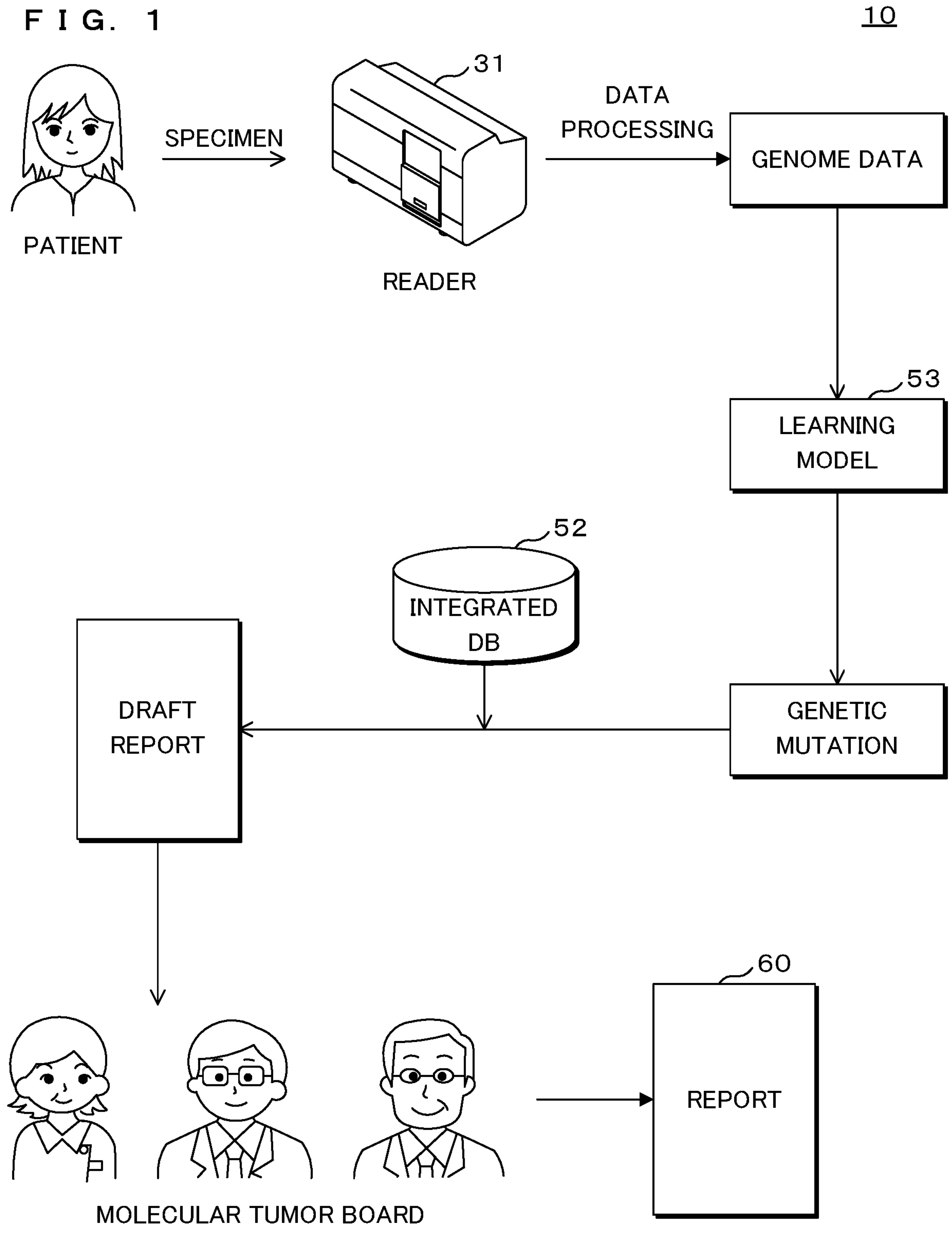
F I G. 1
10
PATIENT
SPECIMEN
31
READER
DATA PROCESSING
GENOME DATA
53
LEARNING MODEL
52
INTEGRATED DB
DRAFT REPORT
GENETIC MUTATION
60
MOLECULAR TUMOR BOARD
REPORT

| SPECIMEN | | GENOME DATA | |
|---|---|---|---|
| NORMAL SPECIMEN | TUMOR SPECIMEN | GENOME DATA FROM NORMAL SPECIMEN | GENOME DATA FROM TUMOR SPECIMEN |
| BLOOD | OVARY | DA001bam<br>DA001.vcf | DB001.bam<br>DB001.vcf |

DIAGNOSIS DATA

| NON-SYNONYMOUS SOMATIC MUTATION | |
|---|---|
| GENE | DNA MUTATION |
| ARID1A | c. 5164C>T |
| TP53 | c. 743G>A |

| GERMLINE MUTATION | |
|---|---|
| GENE | DNA MUTATION |
| BRAF | c. 1791T>G |
| FGFR3 | c. 746C>G |
| MLH1 | c. 1151T>A |

| TUMOR CONTENT [%] |
|---|
| 50 |

FIG. 7

| VERSION |
| --- |
| 2018/9/20 |

52

| GENOME MUTATION | | | KNOWLEDGE DATA | | |
| --- | --- | --- | --- | --- | --- |
| SPECIMEN | GENE | MUTATION CONTENTS | ONCOGENICITY | CLINICAL SIGNIFICANCE | CORRESPONDING MEDICAL AGENT |
| OVARY | BRAF | NON-SYNONYMOUS SOMATIC MUTATION | POTENTIALLY ONCOGENIC MUTATIONS | PATHOGENIC MUTATION | LXH254 |
| OVARY | NF1 | NON-SYNONYMOUS SOMATIC MUTATION | POTENTIALLY ONCOGENIC MUTATIONS | — | — |
| NORMAL SITE | MLH1 | GERMLINE MUTATION | — | PATHOGENIC MUTATION | — |

| CORRESPONDING DISEASE | LEVEL | BASIS INFORMATION |
| --- | --- | --- |
| OVARIAN CANCER | 2 | Genes 28. p.63-81,2018 |
| — | 4 | Medical Journal 321 p1191-1199, 2015 |
| — | 3 | Genes 20. p.120-131,2016 |

| SPECIMEN ID | SPECIMEN | | GENOME DATA | | INTEGRATED DB Ver. |
|---|---|---|---|---|---|
| | NORMAL SPECIMEN | TUMOR SPECIMEN | GENOME DATA FROM NORMAL SPECIMEN | GENOME DATA FROM TUMOR SPECIMEN | |
| 1111111 | BLOOD | OVARY | DA001bam DA001.vcf | DB001.bam DB001.vcf | 2018/6/7 |

DIAGNOSIS DATA

| NON-SYNONYMOUS SOMATIC MUTATION | | | | | | | |
|---|---|---|---|---|---|---|---|
| DIAGNOSIS DATA | | KNOWLEDGE DATA | | | | | |
| GENE | DNA MUTATION | ONCOGENICITY | CLINICAL SIGNIFICANCE | CORRESPONDING MEDICAL AGENT | CORRESPONDING DISEASE | LEVEL | BASIS INFORMATION |
| CTLA4 | c. 196G>T | — | — | — | — | — | ····· |
| TP53 | c. 743G>A | POTENTIALLY ONCOGENIC MUTATIONS | PATHOGENIC MUTATION | — | — | 4 | ····· |
| ZFHX3 | c. 3127A>G | — | — | — | — | — | ····· |

| GERMLINE MUTATION | | | | |
|---|---|---|---|---|
| DIAGNOSIS DATA | | KNOWLEDGE DATA | | |
| GENE | DNA MUTATION | CLINICAL SIGNIFICANCE | LEVEL | BASIS INFORMATION |
| MLH1 | c. 986A>C | PATHOGENIC MUTATION | 3 | ····· |

| TUMOR CONTENT [%] |
|---|
| 20 |

| EXPERT ID |
|---|
| E222 |
| E333 |
| E444 |

F I G. 9
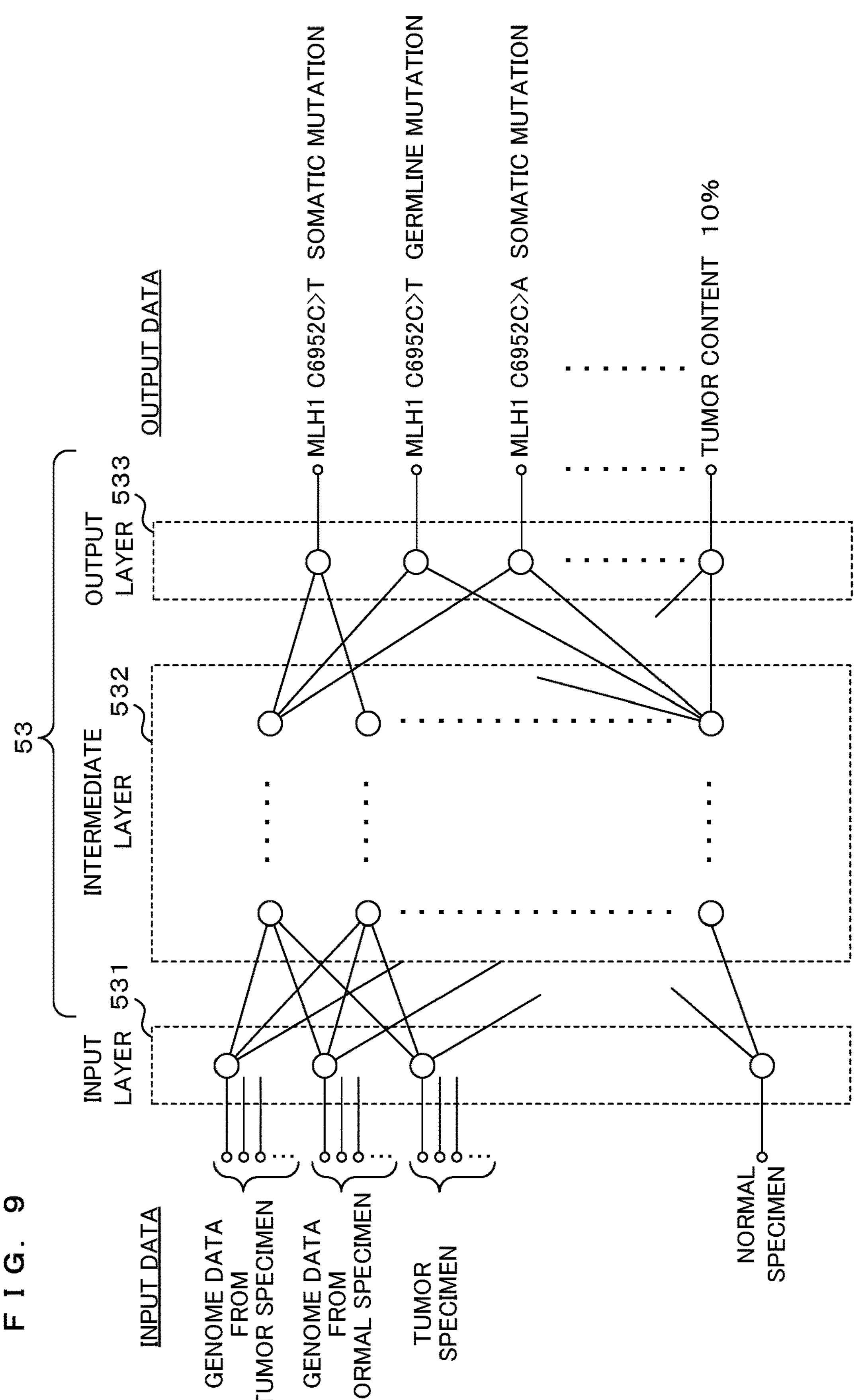

FIG. 11A

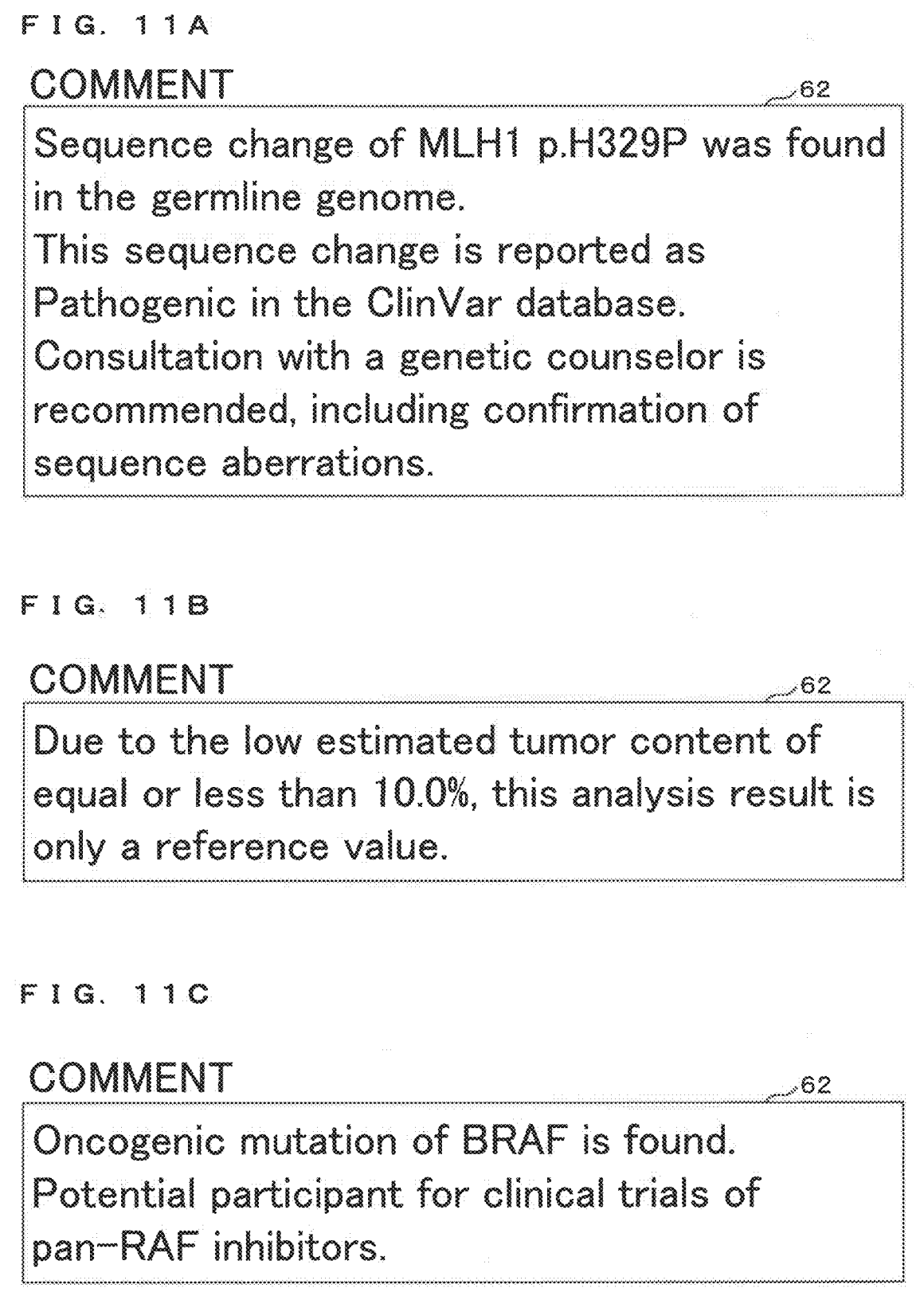

COMMENT

62

Sequence change of MLH1 p.H329P was found in the germline genome.
This sequence change is reported as Pathogenic in the ClinVar database.
Consultation with a genetic counselor is recommended, including confirmation of sequence aberrations.

FIG. 11B

COMMENT

62

Due to the low estimated tumor content of equal or less than 10.0%, this analysis result is only a reference value.

FIG. 11C

COMMENT

62

Oncogenic mutation of BRAF is found.
Potential participant for clinical trials of pan-RAF inhibitors.

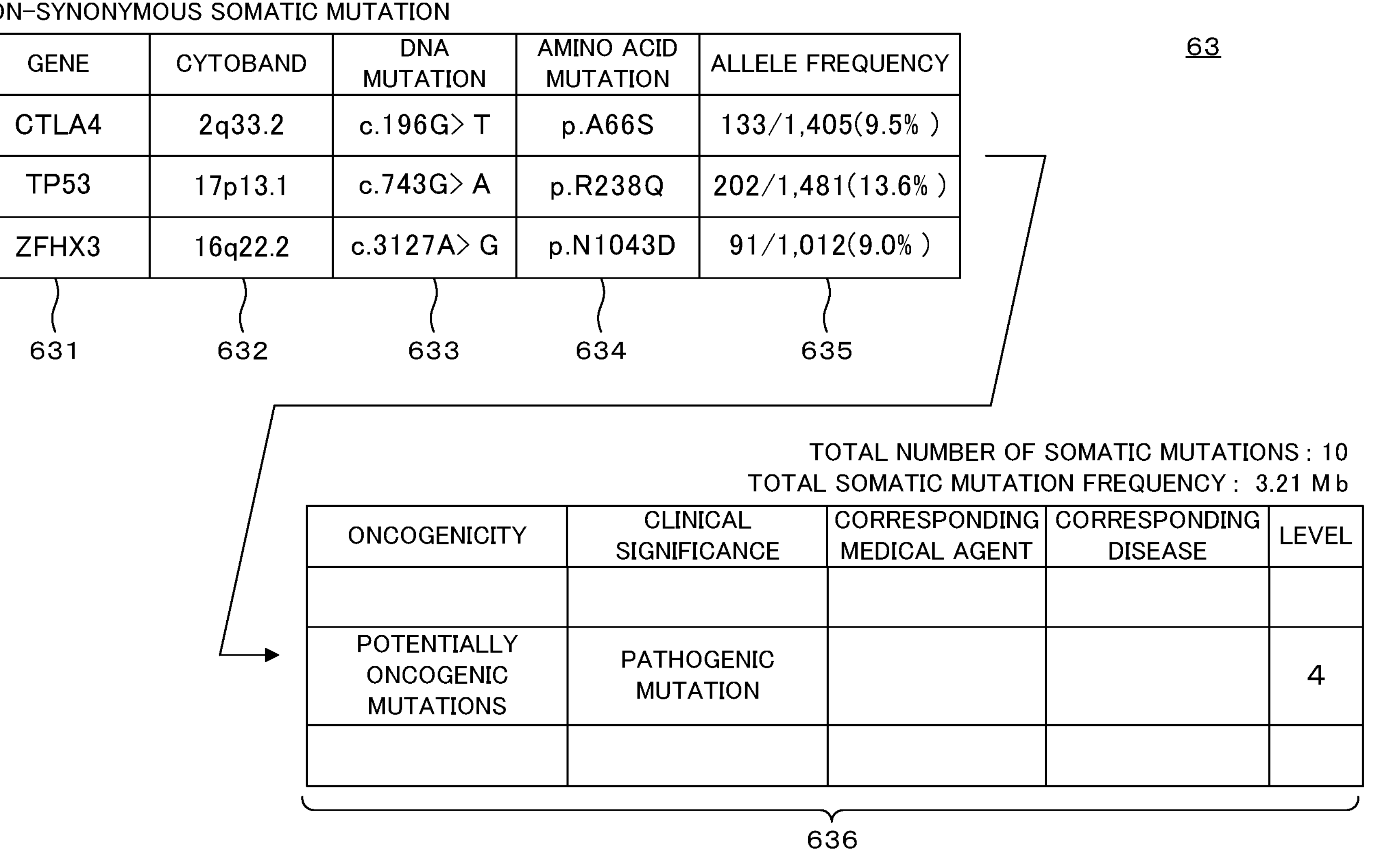
F I G. 1 2
63
NON-SYNONYMOUS SOMATIC MUTATION
GENE
CYTOBAND
DNA MUTATION
AMINO ACID MUTATION
ALLELE FREQUENCY
CTLA4
2q33.2
c.196G>T
p.A66S
133/1,405(9.5%)
TP53
17p13.1
c.743G>A
p.R238Q
202/1,481(13.6%)
ZFHX3
16q22.2
c.3127A>G
p.N1043D
91/1,012(9.0%)
631
632
633
634
635
TOTAL NUMBER OF SOMATIC MUTATIONS : 10
TOTAL SOMATIC MUTATION FREQUENCY : 3.21 Mb
ONCOGENICITY
CLINICAL SIGNIFICANCE
CORRESPONDING MEDICAL AGENT
CORRESPONDING DISEASE
LEVEL
POTENTIALLY ONCOGENIC MUTATIONS
PATHOGENIC MUTATION
4
636

| GENE | CYTOBAND | DNA MUTATION | AMINO ACID MUTATION | NORMAL SITE ALLELE FREQUENCY | TUMOR SITE ALLELE FREQUENCY | CLINICAL SIGNIFICANCE | LEVEL |
|---|---|---|---|---|---|---|---|
| MLH1 | 3p22.2 | c.986A>C | p.H329P | 473/1,009(46.9%) | 293/702 (41.7%) | PATHOGENIC MUTATION | 3 |

ANALYSIS

| ESTIMATED TUMOR CONTENT | MUTATION FREQUENCY CORRELATION COEFFICIENT |
| --- | --- |
| 20.0% | 0.965 ※Normal and tumor specimens were determined to be from the same patient. |

FUSION GENE AND EXON SKIPPING

66

No applicable fusion gene or exon skipping were found.

FIG. 17

| GENOME MUTATION | | | CHANGE DATE | | |
|---|---|---|---|---|---|
| TUMOR SPECIMEN | GENE | MUTATION CONTENTS | FIRST CHANGE DATE | SECOND CHANGE DATE | ······ |
| OVARY | BRAF | NON-SYNONYMOUS SOMATIC MUTATION | 2015/5/1 | 2016/8/5 | ······ |
| OVARY | NF1 | NON-SYNONYMOUS SOMATIC MUTATION | 2015/5/1 | 2016/9/10 | ······ |
| LUNG | TP53 | NON-SYNONYMOUS SOMATIC MUTATION | 2015/5/1 | 2017/12/4 | ······ |
| NORMAL SITE | MLH1 | GERMLINE MUTATION | 2015/5/1 | 2018/3/3 | ······ |

FIG. 18

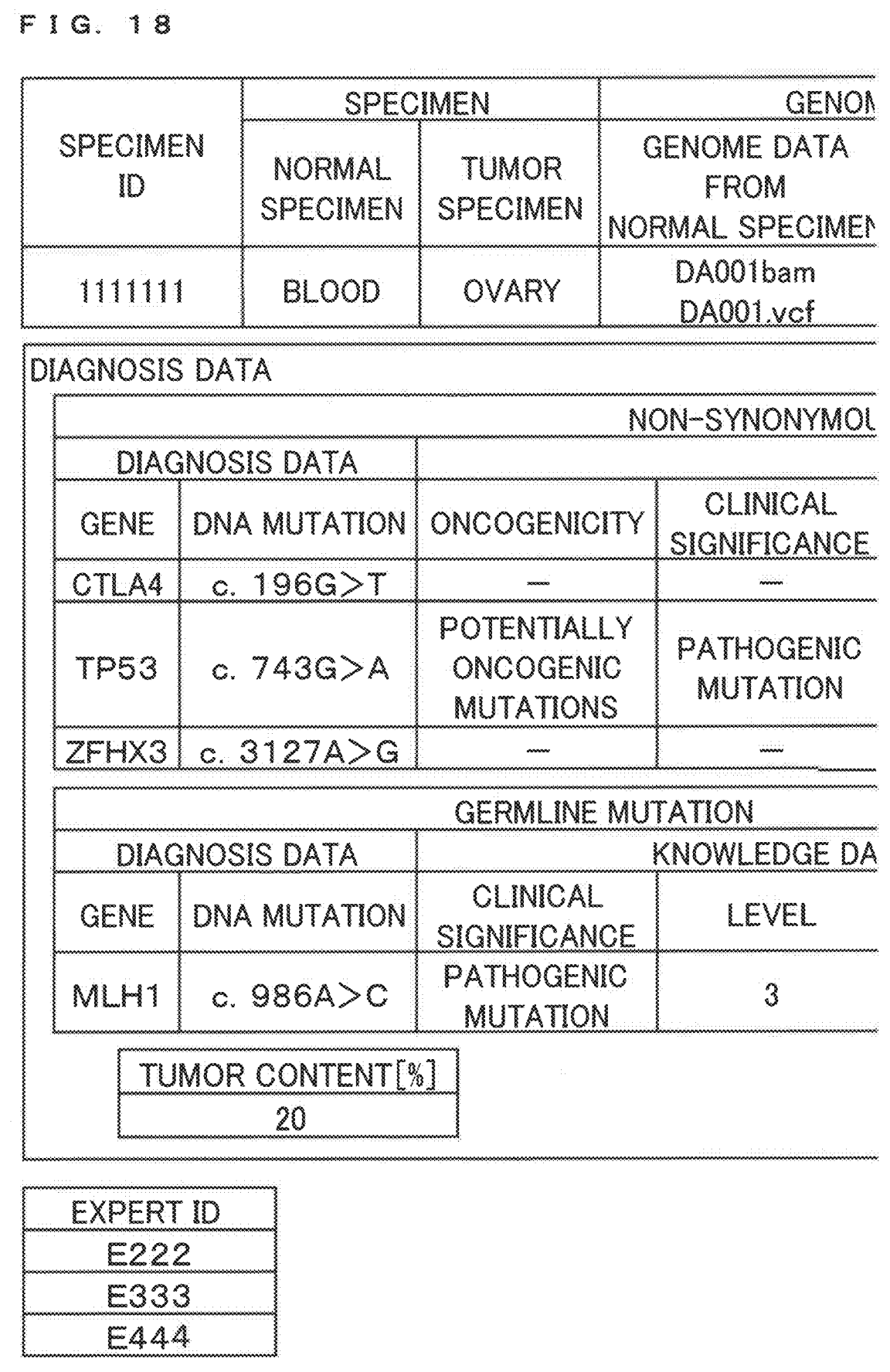

| SPECIMEN ID | SPECIMEN | | GENOM |
|---|---|---|---|
| | NORMAL SPECIMEN | TUMOR SPECIMEN | GENOME DATA FROM NORMAL SPECIMEN |
| 1111111 | BLOOD | OVARY | DA001bam DA001.vcf |

DIAGNOSIS DATA

| NON-SYNONYMOU | | | |
|---|---|---|---|
| DIAGNOSIS DATA | | | |
| GENE | DNA MUTATION | ONCOGENICITY | CLINICAL SIGNIFICANCE |
| CTLA4 | c. 196G>T | — | — |
| TP53 | c. 743G>A | POTENTIALLY ONCOGENIC MUTATIONS | PATHOGENIC MUTATION |
| ZFHX3 | c. 3127A>G | — | — |

| GERMLINE MUTATION | | | |
|---|---|---|---|
| DIAGNOSIS DATA | | KNOWLEDGE DA | |
| GENE | DNA MUTATION | CLINICAL SIGNIFICANCE | LEVEL |
| MLH1 | c. 986A>C | PATHOGENIC MUTATION | 3 |

| TUMOR CONTENT[%] |
|---|
| 20 |

| EXPERT ID |
|---|
| E222 |
| E333 |
| E444 |

Figure 18:
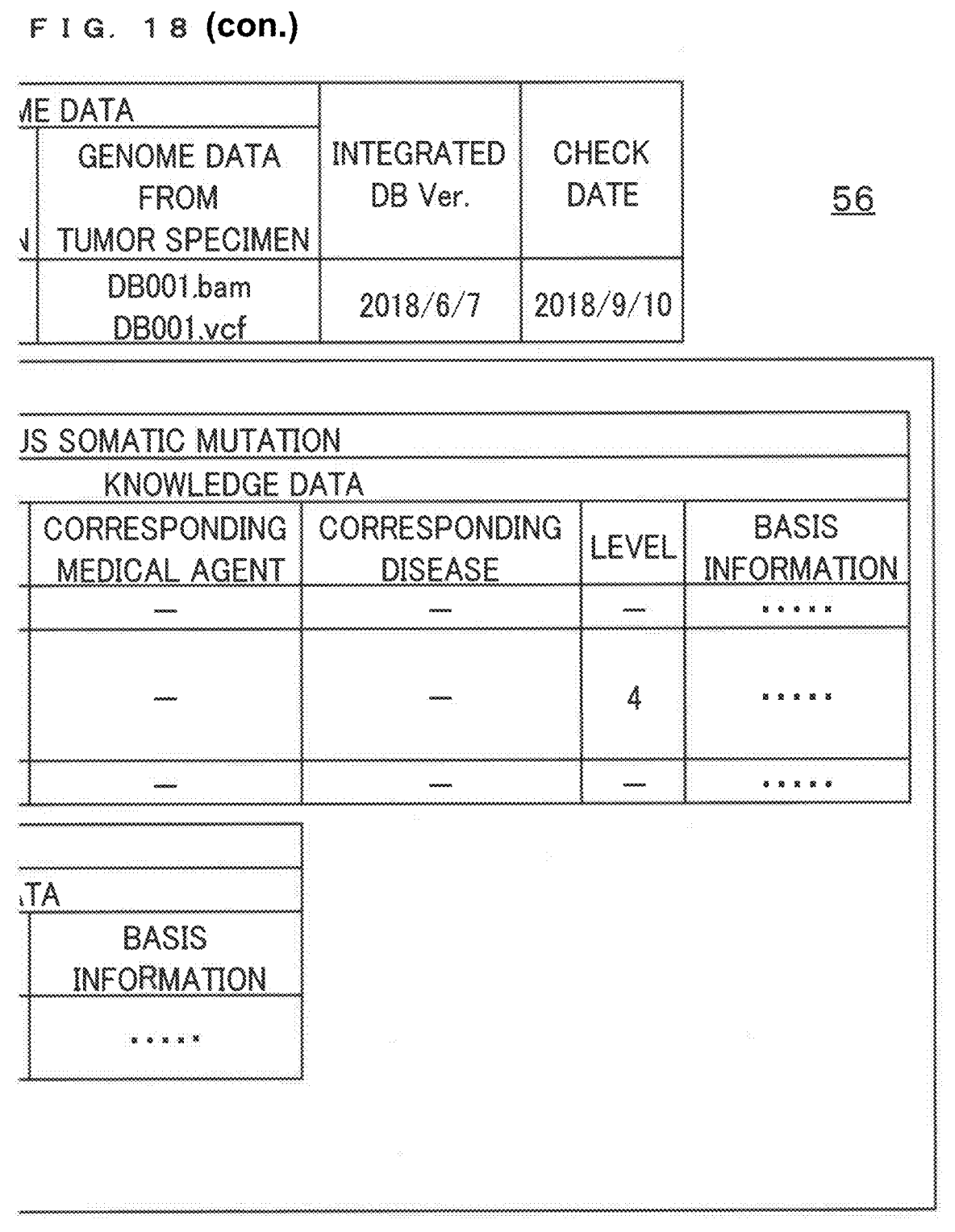

FIG. 18 (con.)

56

| ...ME DATA | | | |
| --- | --- | --- | --- |
| ...N | GENOME DATA FROM TUMOR SPECIMEN | INTEGRATED DB Ver. | CHECK DATE |
| | DB001.bam<br>DB001.vcf | 2018/6/7 | 2018/9/10 |

| ...US SOMATIC MUTATION | | | | |
| --- | --- | --- | --- | --- |
| | KNOWLEDGE DATA | | | |
| | CORRESPONDING MEDICAL AGENT | CORRESPONDING DISEASE | LEVEL | BASIS INFORMATION |
| | — | — | — | ····· |
| | — | — | 4 | ····· |
| | — | — | — | ····· |

| | |
| --- | --- |
| ...TA | |
| | BASIS INFORMATION |
| | ····· |

| EXPERT ID | SPECIALTY AREA | POINT |
|---|---|---|
| E001 | GYNECOLOGIC, OBSTETRIC | 215 |
| E002 | RESPIRATORY | 583 |
| E003 | DIGESTIVE | 123 |

FIG. 21

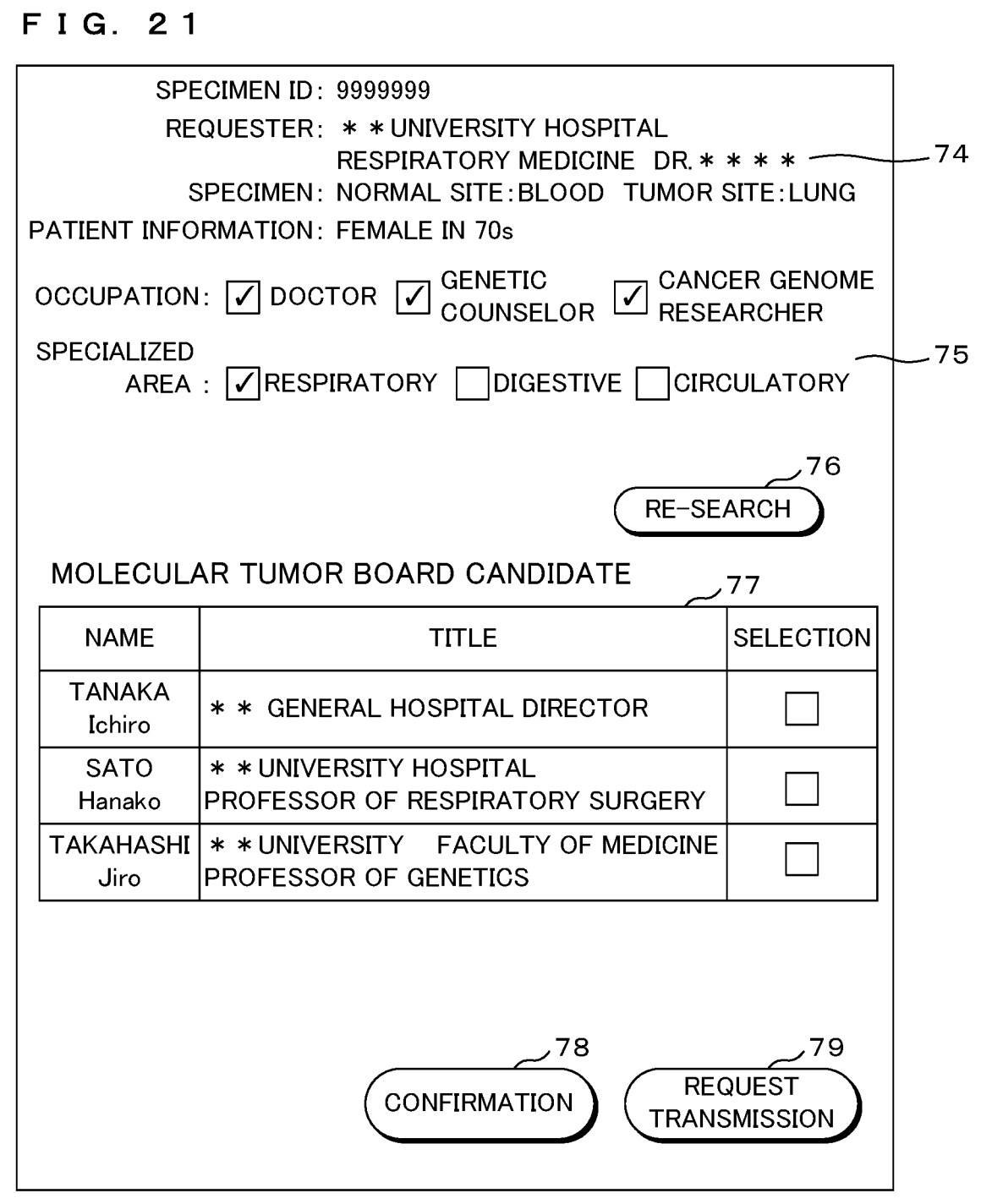

| NAME | TITLE | SELECTION |
|---|---|---|
| TANAKA Ichiro | * * GENERAL HOSPITAL DIRECTOR | ☐ |
| SATO Hanako | * * UNIVERSITY HOSPITAL PROFESSOR OF RESPIRATORY SURGERY | ☐ |
| TAKAHASHI Jiro | * * UNIVERSITY FACULTY OF MEDICINE PROFESSOR OF GENETICS | ☐ |

FIG. 22

MOLECULAR TUMOR BOARD PARTICIPATION REQUEST

72

| No. | SPECIMEN | | PATIENT INFORMATION | MEDICAL INSTITUTION | |
|---|---|---|---|---|---|
| | NORMAL SITE | TUMOR SITE | | | |
| No.1 | BLOOD | LUNG | MALE IN 80s | **UNIVERSITY HOSPITAL RESPIRATORY SURGERY DEPARTMENT | 71 PARTICIPATE |
| No.2 | BLOOD | OVARY | FEMALE IN 40s | **GENERAL HOSPITAL OBSTETRICS AND GYNECOLOGY DEPARTMENT | 71 PARTICIPATE |
| No.3 | BLOOD | UPPER JAW | FEMALE IN 60s | **MUNICIPAL HOSPITAL SURGICAL DEPARTMENT | 71 PARTICIPATE |

FIG. 24

INTEGRATED DB REVIEW REQUEST

73

| No. | GENE | DNA MUTATION | INFORMATION SOURCE | CURRENT DATA |
| --- | --- | --- | --- | --- |
| No.1 | CTLA4 | c.196G>T | Genes 29. p.201-222,2018 | LINK |
| No.2 | MLH1 | c.986A>C | Journal of Genetics 38 p111-119, 2018 | LINK |
| No.3 | – | – | Use of Nivolumab (immune checkpoint inhibitor) | LINK |
| No.4 | FUSION GENE PAX3-FOXO1 | – | About the clinical trial of fusion gene PAX3 | LINK |

71 PARTICIPATE

71 PARTICIPATE

71 PARTICIPATE

NON-TRANSITORY COMPUTER READABLE MEDIUM, INFORMATION PROCESSING DEVICE, INFORMATION PROCESSING METHOD, AND METHOD FOR GENERATING LEARNING MODEL

REFERENCE TO RELATED APPLICATIONS

This application is the national phase under 35 U. S. C. § 371 of International Patent Application PCT/JP2020/028900 which has an International filing date of Jul. 28, 2020, the entire contents of each of which are hereby incorporated by reference.

FIELD OF THE INVENTION

The present invention relates to a program, an information processing device, an information processing method, and a method for generating a learning model.

BACKGROUND ART

A pathological test, a genetic test, or the like is performed using a specimen that is sampled from a patient by a biopsy, a blood collection, or a surgery. In the genetic test, a genomic analysis device or the like that visualizes a base sequence of a nucleic acid read by a sequencer is proposed (for example, refer to International Publication No. 2016-175330).

DESCRIPTION

It is found that the effect of an anticancer agent may be greatly different in accordance with a mutation state of the base sequence. Information about a mutation that contributes to the determination of a therapeutic strategy is important for a clinician handling a medical treatment of a cancer patient.

However, in the genomic analysis device disclosed in Patent Document 1, a clinically important mutation is not capable of being automatically extracted.

A program causing a computer to execute processing of acquiring training data in which genome data obtained by reading a base sequence included in a specimen and a genetic mutation according to the specimen are recorded in association with each other, for a plurality of genetic tests performed in the past, and generating a learning model for outputting a prediction of the genetic mutation based on the specimen in a case where the genome data obtained by reading the base sequence included in the specimen is input by setting the genome data as input and the genetic mutation as output.

In one aspect, an object is to provide a program or the like that automatically extracts a clinically important mutation, on the basis of a base sequence read from a specimen.

The above and further objects and features will more fully be apparent from the following detailed description with accompanying drawings.

FIG. 1 is an explanatory diagram illustrating a flow of processing using a genomic analysis system.

FIG. 6 is an explanatory diagram illustrating a record layout of a training data DB.

FIG. 7 is an explanatory diagram illustrating a record layout of the integrated DB.

FIG. 8 is an explanatory diagram illustrating a record layout of a report DB.

FIG. 9 is an explanatory diagram illustrating the learning model.

FIG. 11A is an explanatory diagram illustrating an example of a comment section.

FIG. 11B is an explanatory diagram illustrating an example of the comment section.

FIG. 11C is an explanatory diagram illustrating an example of the comment section.

FIG. 12 is an explanatory diagram illustrating an example of a non-synonymous somatic mutation section.

FIG. 14 is an explanatory diagram illustrating an example of an analysis section.

FIG. 16A is an explanatory diagram illustrating an example of an RNA section.

FIG. 17 is an explanatory diagram illustrating a record layout of a change history DB.

FIG. 18 is an explanatory diagram illustrating a record layout of a report DB of Embodiment 3.

FIG. 19 is a flowchart illustrating a flow of processing of a program that outputs an additional report.

FIG. 20 is an explanatory diagram illustrating a record layout of an expert DB.

FIG. 21 is an explanatory diagram illustrating an example of a screen for selecting a participant in an molecular tumor board.

FIG. 22 is an explanatory diagram illustrating an example of a screen for checking a participation request for the molecular tumor board.

FIG. 24 is an explanatory diagram illustrating an example of an integrated DB review participation request screen.

EMBODIMENT 1

FIG. 1 is an explanatory diagram illustrating the flow of processing using a genomic analysis system 10. A genome indicates the entire genetic information of one individual, here, one person.

A specimen is sampled from a patient. It is desirable that the specimen is respectively sampled from both of a tumor site and a normal site. The specimen of the tumor site is sampled by a biopsy, a surgery, or the like of a lesion. In the following description, the specimen sampled from the tumor site will be referred to as a tumor specimen. The specimen of the normal site is often sampled by a blood collection or the like, except for a patient having a blood problem such as a blood cancer. In the case of the patient with the blood cancer, the specimen of the tumor site is sampled from the blood, and the specimen of the normal site is sampled from other normal tissues.

A nucleic acid, that is, a deoxyribonucleic acid (DNA) or a ribonucleic acid (RNA) is extracted from each of the specimens. In the following description, a case in which the DNA is extracted will be described as an example. Abase sequence of the DNA is read by a reader 31, and genome data is created. The details of the genome data will be described below. In the following description, a case in which the reader 31 is a next-generation sequencer will be described as an example, but the reader 31 may be an arbitrary device or equipment that reads a DNA microarray and other base sequences.

The genome data is input to a learning model 53. A prediction of a clinically significant genetic mutation is output from the learning model 53. A draft report is automatically created on the basis of the output genetic mutation, and an integrated database (DB) 52 in which information collected from medical literatures or the like are integrated. The details of the learning model 53 and the integrated DB 52 will be described below.

Note that, the prediction of the genetic mutation may be output from the learning model 53 regardless of a clinical significance. In such a case, a clinically significant mutation is extracted on the basis of the genetic mutation output from the learning model 53, and the integrated DB 52, and the draft report is automatically created.

An molecular tumor board including experts such as a cancer expert and a geneticist reviews the draft report, and corrects the draft report as necessary, and thus, a report is completed. A clinician handling a medical treatment of a patient determines a therapeutic strategy by the report. The details of the draft report and the report will be described below. Note that, the molecular tumor board may not review the draft report. In such a case, the clinician determines the therapeutic strategy by the draft report output from the integrated DB 52.

Figure 2:
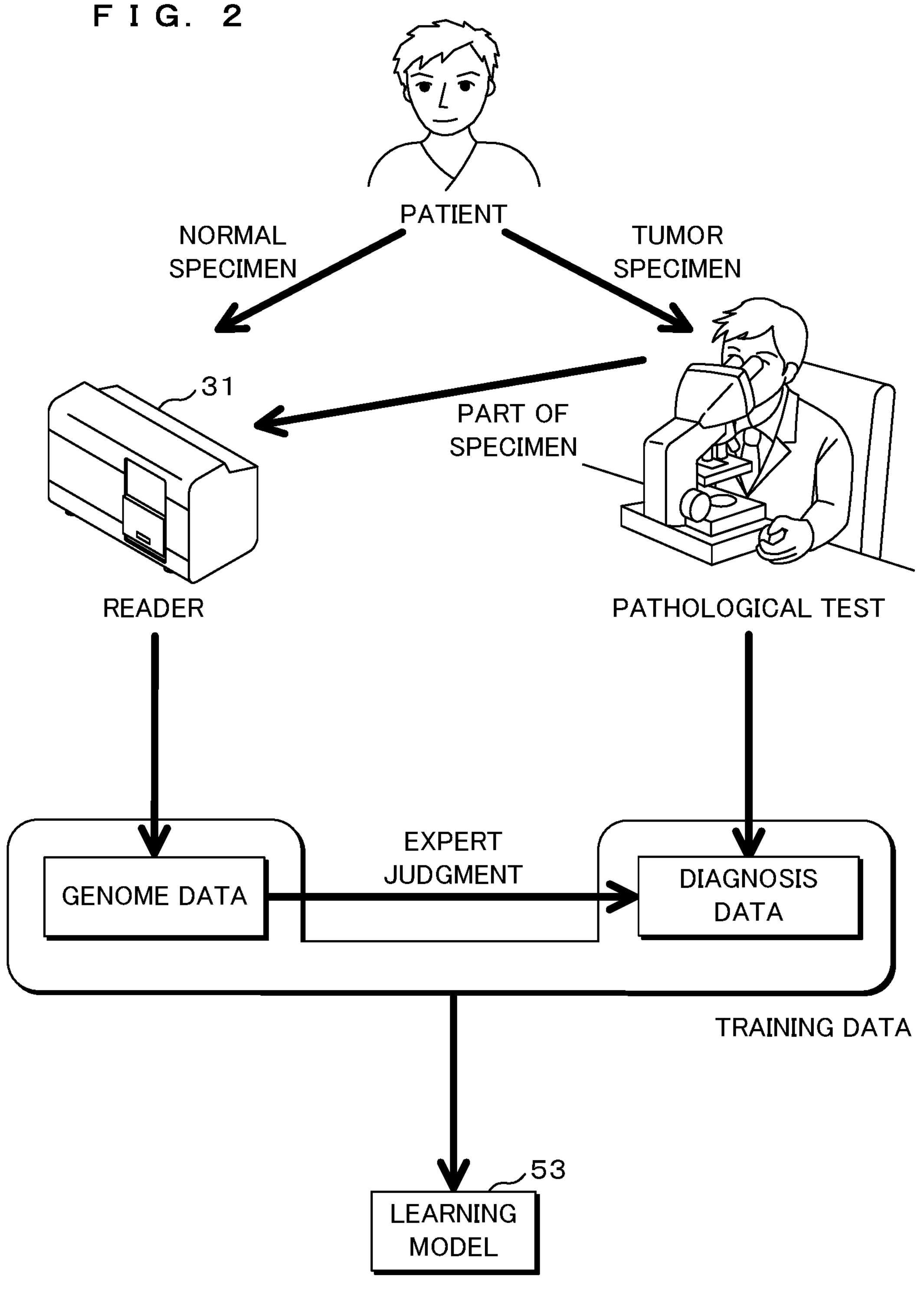
FIG. 2 is an explanatory diagram illustrating a method for generating a learning model.

FIG. 2 is an explanatory diagram illustrating a method for generating the learning model 53. A pathological test is performed using the specimen of the tumor site. A part including the tumor cell is cut out from the specimen of the tumor site. The DNA of the tumor site is extracted from the cut specimen. The DNA of the normal site is extracted from the specimen of the normal site. The DNA of the normal site and the DNA of the tumor site are put in the reader 31, and the genome data is created.

The expert determines the malignity or benignancy of a tumor, whether the tumor is an original cancer, a tumor content in the specimen of the tumor site, a medical agent that can be expected to be effective, and the like, on the basis of the result of the pathological test, the genome data, and the other test values, and creates diagnosis data.

In a training data DB 51 (refer to FIG. 5), the genome data and the diagnosis data are recorded in association with each other. The details of the training data DB 51 will be described below. Supervised machine learning is performed on the basis of the training data DB 51, and the learning model 53 is generated. In a case where the genome data obtained by reading the base sequence included in the specimen is input, the learning model 53 is a learned model for outputting the prediction of the genetic mutation according to the specimen.

Figure 3:
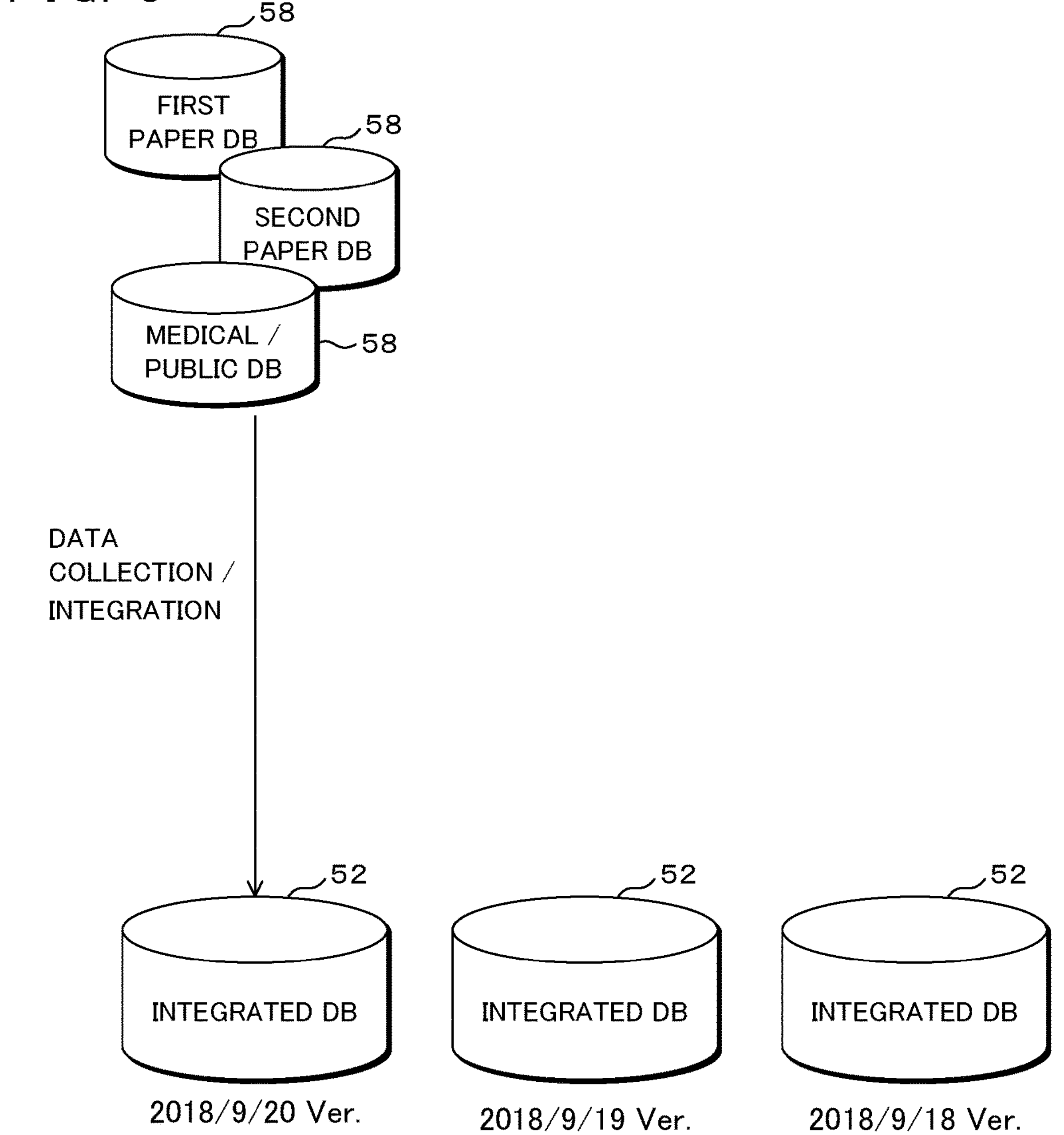
FIG. 3 is an explanatory diagram illustrating an outline of an integrated DB.

FIG. 3 is an explanatory diagram illustrating the outline of the integrated DB 52. The integrated DB 52 is a DB in which medical information about the genetic mutation acquired from a plurality of information sources, and an acquisition source of the medical information are integrated in association with each other. The information source, for example, is various medical information DBs 58 such as a DB in which medical papers are published, a DB in which the government, a research institution, or the like publishes information on a clinical trial of a medical agent or a therapeutic method, and a DB in which public information such as press release on a medical procedure published by a company, a university, or the like is accumulated.

The medical information DB 58 may be a DB that is published without charge, or may be a DB that is published with charge. Note that, in the case of using the DB that is published with charge, license processing such as signing a suitable license contract between a provider of the paid DB and a provider of the integrated DB 52 is performed.

In each of the medical information DBs 58, the medical information is recorded in different formats, and the information is updated at different timings. The integrated DB 52 is created by crawling of accessing each of the medical information DBs 58 and collecting the information to compile a database.

The crawling is suitably performed, and the updated integrated DB 52 is created. The version of each of the integrated DBs 52, for example, is managed in a state where an update date, an update date and time, or the like can be discriminated. The details of the integrated DB 52 will be described below.

Note that, each of the integrated DBs 52 may be configured such that a difference from the previous version or a different from an arbitrary version can be recorded, and as necessary, the integrated DB 52 at an arbitrary point can be constructed. By recording the difference, a recording capacity of the integrated DB 52 can be saved.

Figure 4:
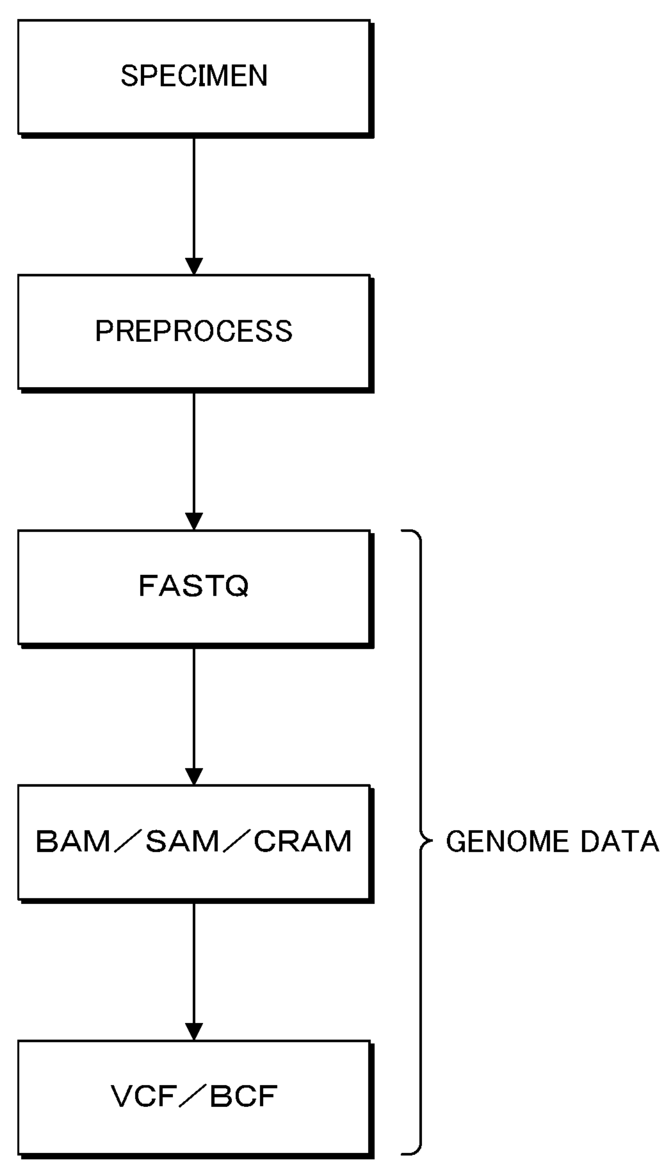
FIG. 4 is an explanatory diagram illustrating an outline of genome data.

FIG. 4 is an explanatory diagram illustrating the outline of the genome data. Preprocessing is performed with respect to the specimen. Specifically, as described above, the DNA is extracted from the specimen. Processing such as purification, fragmentation, and amplification is performed with respect to the extracted DNA. By the fragmentation, the DNA is cut into a fragment having a length suitable for the reading of the reader 31 that is used in the subsequent step.

The reader 31 sequentially reads the base sequence of each of the fragmented DNAs. Information on the base sequence read from one DNA fragment will be referred to as a read. In the read, a quality score indicating a reading reliability with respect to each of the bases is also recorded.

Each of the reads, for example, is mapped in a reference sequence such as a Japanese reference genome (JRG) or an international human genome reference sequence. A mapping result, for example, is recorded in a file in a BAM (Binary Sequence Alignment Map) format, a SAM (Sequence Alignment Map) format, or a CRAM (Compressed Reference-oriented Alignment Map) format.

Information on a difference between the mapping result and the reference sequence, that is, the position of a part in which the genome of the specimen is mutated with respect to the reference sequence, mutation contents, and the like, for example, is recorded in a file in a VCF (Variant Call Format) format or a BCF (Binary Variant Call Format) format.

Note that, in the file in the VCF format, a plurality of mutations with low clinical importance, such as the mutation of an intron in which genetic information is not coded, and a synonymous mutation in which a coded amino acid is not changed, are included. Therefore, an advanced technical knowledge is required to read information for setting the therapeutic strategy or the like from the file in the VCF format.

In a case where a file in a FASTQ format and the reference sequence are given, the file in the FASTQ format can be converted into the file in the BAM format, the SAM format, the CRAM format, and the VCF format by a known analysis method. The data in the FASTQ format, the BAM format, the SAM format, the CRAM format, the VCF format, and the BCF format described above will be collectively referred to as the genome data. The genome data may be data in an arbitrary format other than the formats exemplified here.

For example, the reader 31 outputs the file in the FASTQ format, and an analysis device not illustrated converts the file in the FASTQ format into the file in the BAM format and the VCF format. The reader 31 may include a built-in analysis device, and may directly output the file in the BAM format and the VCF format. An information processing device 20 (refer to FIG. 5) described below may acquire the file in the FASTQ format or the BAM format, and may convert the file in the FASTQ format or the BAM format into the file in the VCF format.

In the case of performing copy number alteration (CNA: body cell copy number aberration) analysis, the genome data obtained from the specimens of a plurality of normal sites sampled from the patient is compared with the genome data obtained from the specimen of the tumor site.

In the CNA analysis, a method of a panel of normals (PON) may be used. In the case of using the PON, for example, the genome data in the BAM format or the SAM format is created and stored for the specimens of the normal sites sampled from a plurality of people. Analysis is performed by comparing the genome data obtained from the specimen of the tumor site sampled from the patient with the stored genome data.

Figure 5:
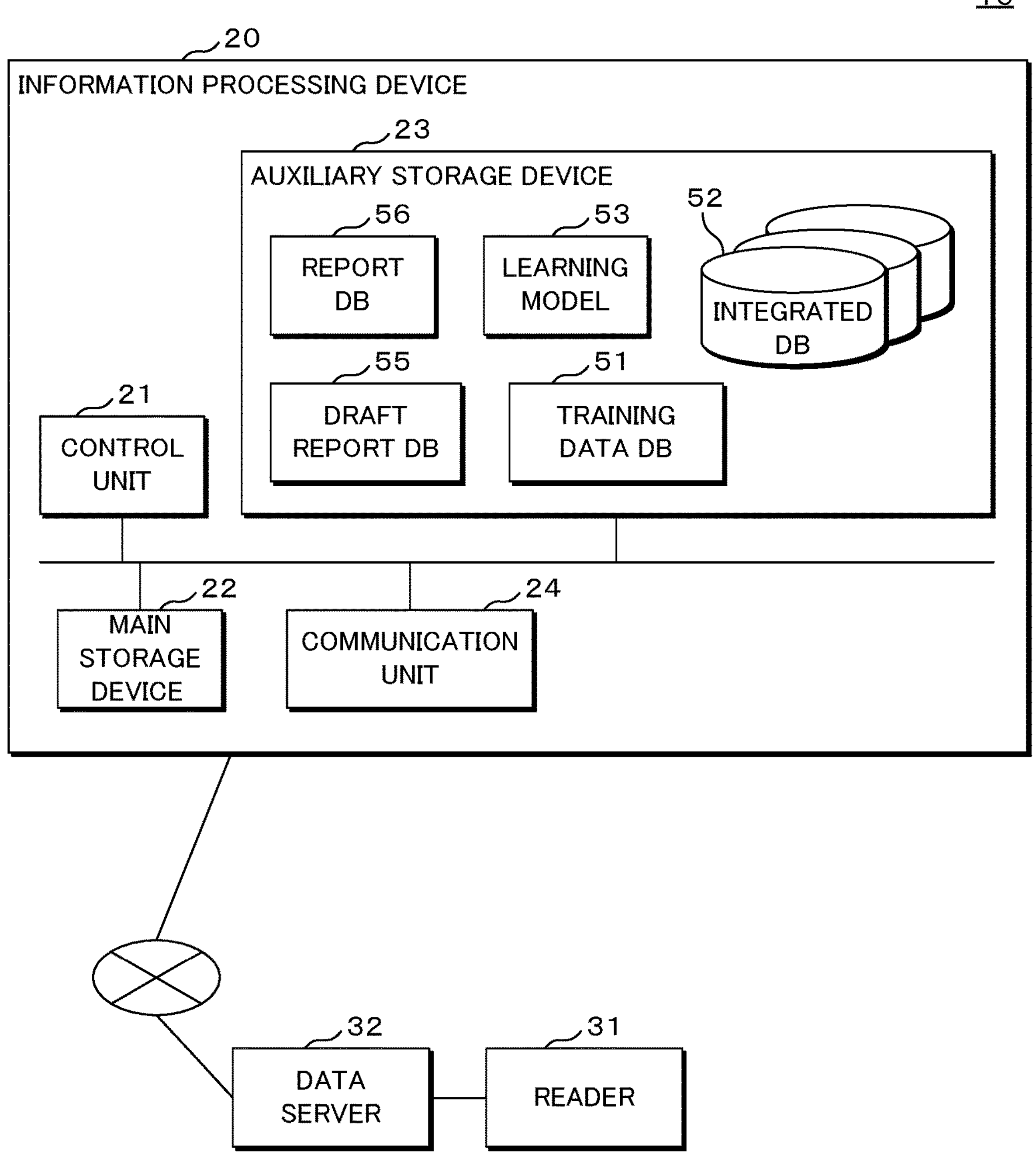
FIG. 5 is an explanatory diagram illustrating a configuration of the genomic analysis system.

FIG. 5 is an explanatory diagram illustrating the configuration of the genomic analysis system 10. The genomic analysis system 10 includes the information processing device 20, the reader 31, and a data server 32.

The information processing device 20 includes a control unit (processor) 21, a main storage device 22, an auxiliary storage device 23, a communication unit 24, and a bus. The control unit 21 is a computation control device that executes a program of this embodiment. The control unit 21 includes one or a plurality of central processing units (CPU), a multi-core CPU, a graphics processing unit (GPU), or the like. The control unit 21 is connected to each hardware unit configuring the information processing device 20 through the bus.

The main storage device 22 is a storage device such as a static random access memory (SRAM), a dynamic random access memory (DRAM), and a flash memory. In the main storage device 22, information required in the middle of the processing of the control unit 21 and the program that is being executed by the control unit 21 are transitorily stored.

The auxiliary storage device 23 is a storage device such as a SRAM, a flash memory, or a hard disk. In the auxiliary storage device 23, the training data DB 51, the integrated DB 52, the learning model 53, a draft report DB 55, a report DB 56, the program that is executed by the control unit 21, and various data pieces required for the execution of the program are stored. Note that, the training data DB 51, the integrated DB 52, the learning model 53, the draft report DB 55, and the report DB 56 may be stored in an external high-capacity storage device connected to the information processing device 20, the data server 32, or the like.

The communication unit 24 is an interface that performs communication between the information processing device 20 and a network.

As described above, the reader 31 is the next-generation sequencer, or the arbitrary device or equipment that reads the DNA microarray and the other base sequences. The genome data created on the basis of the base sequence read by the reader 31 is recorded in the data server 32. The control unit 21 is capable of acquiring the genome data recorded in the data server 32 through the communication unit 24 and the network. Note that, the control unit 21 may directly acquire the genome data from the reader 31 without using the data server 32.

The information processing device 20 of this embodiment is a general-purpose personal computer, a tablet, a large-size computing machinery, or a virtual machine that is operated on the large-size computing machinery. The information processing device 20 may include hardware such as a plurality of personal computers, tablets, or large-size computing machineries. The information processing device 20 may include a quantum computer. The information processing device 20 may be integrated with the reader 31. The information processing device 20 may be attained by so-called cloud computing.

FIG. 6 is an explanatory diagram illustrating a record layout of the training data DB 51. The training data DB 51 is a DB in which the genome data and the diagnosis data are recorded in association with each other. In FIG. 6, one record of the training data DB 51 is illustrated.

The training data DB 51 includes a specimen field, a genome data field, and a diagnosis data field. The specimen field includes a normal site specimen field and a tumor site specimen field. The genome data field includes a genome data from normal specimen field and a genome data from tumor specimen field. Note that, the training data DB 51 may not include the genome data from normal specimen field.

The diagnosis data field includes a non-synonymous somatic mutation field, a germline mutation field, and a tumor content field. The non-synonymous somatic mutation field includes a gene field and a DNA mutation field. The germline mutation field includes a gene field and a DNA mutation field. The training data DB 51 includes one record for one pair of training data pieces. Note that, the diagnosis data field may not include the tumor content field.

In the normal site specimen field, a region in which the specimen of the normal site is sampled is recorded. In the tumor site specimen field, a region in which the specimen of the tumor site is sampled is recorded. In the genome data from normal specimen field, a file name of the genome data acquired from the normal site specimen is recorded. In the genome data from tumor specimen field, a file name of the genome data acquired from the tumor site specimen is recorded.

In a subfield of the non-synonymous somatic mutation field, a gene having a non-synonymous somatic mutation included in the genome of the tumor site, that is, a somatic mutation in which an amino acid coded in the base sequence of the DNA is changed, and mutation contents are recorded. The somatic mutation indicates a mutation that does not occur in the genome of the normal site but occurs in the genome of the tumor site. That is, the non-synonymous somatic mutation is a mutation relevant to the properties of the tumor.

For example, the first row of the non-synonymous somatic mutation field in FIG. 6 indicates that the 5164-th base of an AT-rich interactive domain 1A (ARID1A) gene is mutated into thymine (T) from cytosine (C). Similarly, the second row indicates that the 743-th base of a TP53 gene is mutated into adenine (A) from guanine (G).

In a subfield of the germline mutation field, a gene having a mutation included in the genome of the normal site, and mutation contents are recorded. For example, the first row of the germline mutation field in FIG. 6 indicates that the 1791-th base of a BRAF gene is mutated into G from T.

In the non-synonymous somatic mutation field and the germline mutation field, an arbitrary number of genes required to be recorded in the training data among the genetic mutations detected from the specimen are recorded.

Note that, the reference sequence such as the Japanese reference genome may be used instead of acquiring the genome data by sampling the specimen of the normal site. In such a case, a result of the germline mutation is an estimation result.

The diagnosis data field may include a synonymous somatic mutation field in which a synonymous somatic mutation is recorded. A somatic mutation field may be provided instead of the non-synonymous somatic mutation field, and both of the synonymous somatic mutation and the non-synonymous somatic mutation may be recorded.

In the tumor content field, the tumor content in the specimen sampled from the tumor site is recorded. The tumor content, for example, is calculated on the basis of a hetero single nucleotide polymorphism (SNP) number. The tumor content may be calculated on the basis of an allele frequency recorded in the BAM file or the SAM file, or an allele frequency calculated from the data recorded in the BAM file or the SAM file.

The tumor content may be calculated on the basis of a ratio of the number of nucleated cells and the number of tumor cells observed by the pathological test, or the area of the tumor cell in the field of a microscope. The definition of the tumor content is arbitrary, but it is desirable that the unified definition is used in all the training data included in the training data DB 51.

FIG. 7 is an explanatory diagram illustrating a record layout of the integrated DB 52. The integrated DB 52 is a DB in which the medical information about the genetic mutation acquired from the plurality of information sources, and the acquisition source of the medical information are integrated in association with each other. The integrated DB 52 includes a version field, a genome mutation field, and a knowledge data field.

In the version field, the version of the integrated DB 52 is recorded. In this embodiment, the integrated DB 52 is managed by the update date.

The genome mutation field includes a specimen field, a gene field, and a mutation contents field. The knowledge data field includes a oncogenicity field, a clinical significance field, a corresponding medical agent field, a corresponding disease field, a level field, and a basis information field. The integrated DB 52 includes one record for one medical information piece about the genetic mutation.

In the specimen field, a region in which the specimen is sampled is recorded. In the gene field, a gene in which a mutation is detected is recorded. Note that, in a record in which medical information about a combination of a plurality of mutations is recorded, a plurality of genes are recorded in the gene field.

In the mutation contents field, the contents of the mutation such as the non-synonymous somatic mutation or the germline mutation are recorded. Note that, information about the synonymous somatic mutation in which the coded amino acid is not changed may be recorded in the integrated DB 52.

In the oncogenicity field, a oncogenicity level of the genome mutation is recorded. In the clinical significance field, a clinical significance of the genome mutation is recorded. The knowledge data field may include only one of the oncogenicity field and the clinical significance field.

In the corresponding medical agent field, a medical agent that is effective in the case of being administered in a patient with a genome mutation is recorded. In the corresponding medical agent field, a medical agent under a therapeutic trial may be recorded. In the corresponding disease field, a disease corresponding to the genome mutation is recorded. In the level field, an importance level of the genome mutation is recorded. In the basis information field, information for accessing basis information, such as a literature on which the information described in the record is based, a database name, or an identifier (ID) uniquely assigned to the information, is recorded.

In each subfield of the knowledge data field, "–" indicates that there is no corresponding information.

FIG. 8 is an explanatory diagram illustrating a record layout of the report DB 56. The report DB 56 is a DB in which information on the specimen and diagnosis data based on the specimen are recorded in association with each other. In FIG. 8, one record of the report DB 56 is illustrated.

The report DB 56 includes a specimen ID field, a specimen field, a genome data field, an integrated DB Ver. field, a diagnosis data field, and an expert ID field. The specimen field includes a normal site specimen field and a tumor site specimen field. The genome data field includes a genome data from normal specimen field and a genome data from tumor specimen field.

The diagnosis data field includes a non-synonymous somatic mutation field, a germline mutation field, and a tumor content field. The non-synonymous somatic mutation field includes a diagnosis data field and a knowledge data field. The diagnosis data field includes a gene field and a DNA mutation field. The knowledge data field includes a oncogenicity field, a clinical significance field, a corresponding medical agent field, a corresponding disease field, a level field, and a basis information field.

The germline mutation field includes a diagnosis data field and a knowledge data field. The diagnosis data field includes a gene field and a DNA mutation field. The knowledge data field includes a clinical significance field, a level field, and a basis information field. The report DB 56 includes one record for one pair of specimens.

In the specimen ID field, a specimen ID uniquely assigned to one pair of specimens is recorded. The specimen ID is associated with the patient, in cooperation with an electronic health record system or the like. In the normal site specimen field, the region in which the specimen of the normal site is sampled is recorded. In the tumor site specimen field, the region in which the specimen of the tumor site is sampled is recorded. In the genome data from normal specimen field, the file name of the genome data acquired from the normal site specimen is recorded. In the genome data from tumor specimen field, the file name of the genome data acquired from the tumor site specimen is recorded. In the integrated DB Ver. field, the version of the integrated DB 52 used when writing a report record is recorded.

In a subfield of the diagnosis data field in the non-synonymous somatic mutation field, the gene having the non-synonymous somatic mutation, and the mutation contents are recorded. In each subfield of the knowledge data field, medical information about the genetic mutation recorded in the diagnosis data field is recorded. The information recorded in each subfield is the same as the information recorded in the subfield with the same name in the integrated DB 52 described using FIG. 7, and thus, the description thereof will be omitted.

In a subfield of the diagnosis data field in the germline mutation field, the gene having the germline mutation, and the mutation contents are recorded. In each subfield of the knowledge data field, the medical information about the genetic mutation recorded in the diagnosis data field is recorded. The information recorded in each subfield is the same as the information recorded in the subfield with the same name in the integrated DB 52 described using FIG. 7, and thus, the description thereof will be omitted.

In the expert ID field, an expert ID uniquely assigned to each of the experts configuring the molecular tumor board who has reviewed the draft report that is automatically created by the control unit 21 with a program described below is recorded. One expert ID may be assigned to an expert group in which a plurality of experts participates.

The record layout of the draft report DB 55 is the same as the record layout of the report DB 56 described using FIG. 8, except that the expert ID field is not provided, and thus, the illustration and the detailed description thereof will be omitted.

FIG. 9 is an explanatory diagram illustrating the learning model 53. The learning model 53 is a neural network including an input layer 531, an intermediate layer 532, and an output layer 533. In FIG. 9, a case is exemplified in which the learning model 53 is CNN. Note that, a convolution layer and a pooling layer are not illustrated.

The input of the learning model 53 is the genome data of the tumor site, the genome data of the normal site, the region in which the specimen of the tumor site is sampled, and the region in which the specimen of the normal site is sampled. The genome data, for example, is a tensor of piled-up alignment information, and includes the base sequence, strand information, base quality, map quality, and the like as constituents. The base sequence may be represented by the count of each base of A, T, G, and C. The data input to the learning model 53 is input to the input layer 531 through the repetition of the convolution layer and the pooling layer, which are not illustrated.

The output of the learning model 53, for example, is the probability of each item of the diagnosis data. Specifically, the output of the learning model is a probability that each clinically significant mutation occurs, and a probability that the tumor content is a predetermined value. For example, in FIG. 9, a probability that a somatic mutation occurs in which the 6952-th base of a BRCA gene is mutated into T from C is output to the top output node, and a probability that a germline mutation occurs in which the 6952-th base of the BRCA gene is mutated into T from C is output to the second output node.

Note that, since the body cell includes an allelic gene, the body cell of the specimen includes the "6952-th base of the BRCA gene" from the father and the "6952-th base of the BRCA gene" from the mother. Therefore, the mutation of the body cell includes a case where both of a gene from the father and a gene from the mother are mutated, a case where only the gene from the father is mutated, and a case where only the gene from the mother is mutated.

For example, the output of the learning model 53 may be the score of HomoRef, Hetero, and HomoAlt. HomoRef, Hetero, and HomoAlt are an index that is used for a variant caller for genomic analysis such as deepvariant.

A probability that the tumor content is 10 percent is output to the bottom output node in FIG. 9. The output node, for example, includes a node to which a probability that the tumor content is an arbitrary tumor content such as the increment of 10 percent is output.

In a case where the genome data and the specimen sample region are input to the input layer 531, the learning model 53 outputs a probability that each clinically significant mutation occurs and the tumor content is the predetermined tumor content to the output layer 533. In a learning stage, the control unit 21 computes parameters of the intermediate layer 532 by a backpropagation method or the like using the training data DB 51 in which the genome data and the specimen sample region, and the presence or absence of the clinically significant mutation and the diagnosis data about the tumor content are recorded in association with each other, and thus, performs supervised machine learning.

The supervised machine learning, for example, can be performed by an arbitrary method such as logistic regression, a support vector machine (SVM), random forests, CNN, RNN, or eXtreme gradient boosting (XGBoost).

The learning model 53 may be generated using an arbitrary computer. The generated learning model 53 is transmitted to the information processing device 20 through a network or the like, and is recorded in the auxiliary storage device 23. Semi-supervised learning may be used instead of the supervised learning.

Figure 10:
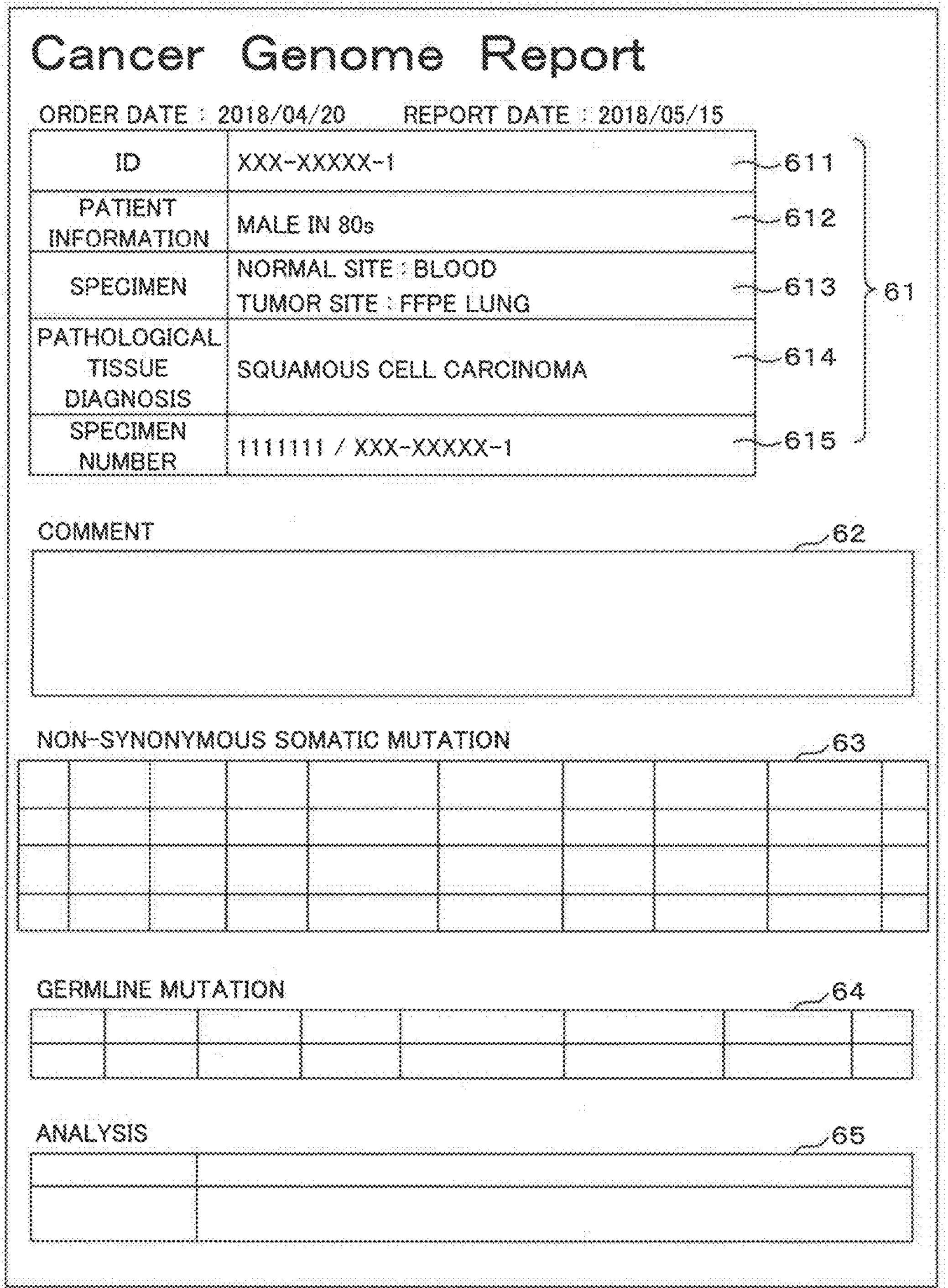
FIG. 10 is an explanatory diagram illustrating an example of a report.

FIG. 10 is an explanatory diagram illustrating an example of a report 60. In the report 60, the information recorded in the record of the report DB 56 and the information recorded in the electronic health record are created by being preformatted in a user-friendly format. The report 60 includes a bibliographic item section 61, a comment section 62, a non-synonymous somatic mutation section 63, a germline mutation section 64, and an analysis section 65.

The bibliographic item section 61 includes an ID section 611, a patient information section 612, a specimen section 613, a pathological tissue diagnosis section 614, and a specimen number section 615. In the ID section 611, a patient ID uniquely assigned to the patient is displayed. In the patient information section 612, the gender and the age of the patient are displayed. Note that, the patient information section 612 may not be displayed.

In the specimen section 613, the specimen of the normal site and the specimen of the tumor site using the genomic analysis are displayed. In FIG. 10, a "formalin fixed paraffin embedded (FFPE) lung" indicates a formalin fixed paraffin embedded lung tissue.

In the pathological tissue diagnosis section 614, an observation according to pathological diagnosis of observing the specimen with a microscope is displayed. In the specimen number section 615, a specimen number uniquely assigned to the specimen is displayed. Information displayed in the bibliographic item section 61 is acquired from the electronic health record system by setting the specimen ID of the report record described using FIG. 8 as a key.

FIG. 11A, FIG. 11B, and FIG. 11C are explanatory diagrams illustrating an example of the comment section 62. FIG. 11A to FIG. 11C illustrate examples of the comment sections 62 that are displayed in reports different from each other, respectively. FIG. 11A illustrates the comment section 62 of a report on a specimen in which a "Pathologic" germline mutation, that is, a germline mutation reliably having pathogenicity is found. A gene in which the germline mutation with pathogenicity occurs and a mutation position, the basis thereof, and advice on the future countermeasure for the germline mutation are displayed.

FIG. 11B illustrates an example of a comment of a report about a specimen in which the tumor content is low, that is, the specimen of the tumor site may have a problem with the quality. FIG. 11C illustrates an example of a comment about a specimen in which an oncogenic mutation is found in the specimen of the tumor site. Information on a gene in which a somatic mutation related to oncogenesis occurs, and a clinical trial on the gene is displayed.

A text displayed in the comment section 62 is created in combination with a fixed phrase by a known method, on the basis of the information recorded in the diagnosis field of the report DB 56. A fixed phrase on a genetic mutation with high pathogenicity or oncogenicity among a plurality of genetic mutations that occur in the specimen is selected and displayed, and thus, even a clinician with little knowledge in a genetic test is capable of promptly grasping information with high importance.

FIG. 12 is an explanatory diagram illustrating an example of the non-synonymous somatic mutation section 63. In FIG. 12, an example of the non-synonymous somatic mutation section 63 that is displayed on the basis of the non-synonymous somatic mutation field in the report record exemplified in FIG. 8 is illustrated.

The non-synonymous somatic mutation section 63 includes a gene section 631, a cytoband section 632, a DNA mutation section 633, an amino acid mutation section 634, an allele frequency section 635, and a knowledge data section 636. In each of the gene section 631, the DNA mutation section 633, and the knowledge data section 636, the information recorded in the non-synonymous somatic mutation field is displayed.

In the cytoband section 632, the position of a gene on a chromosome is displayed. In the amino acid mutation section 634, the mutation of an amino acid due to a DNA mutation is displayed. In the allele frequency section 635, for example, the allele frequency recorded in the BAM file or the SAM file or the allele frequency calculated from the data recorded in the BAM file or the SAM file is displayed.

In the upper portion of the non-synonymous somatic mutation section 63, the total number of somatic mutations also including a somatic mutation that is not described in the non-synonymous somatic mutation section 63 and a total somatic mutation frequency are displayed. The total number of somatic mutations and the total somatic mutation frequency can be acquired from the file in the VCF format.

Figure 13:
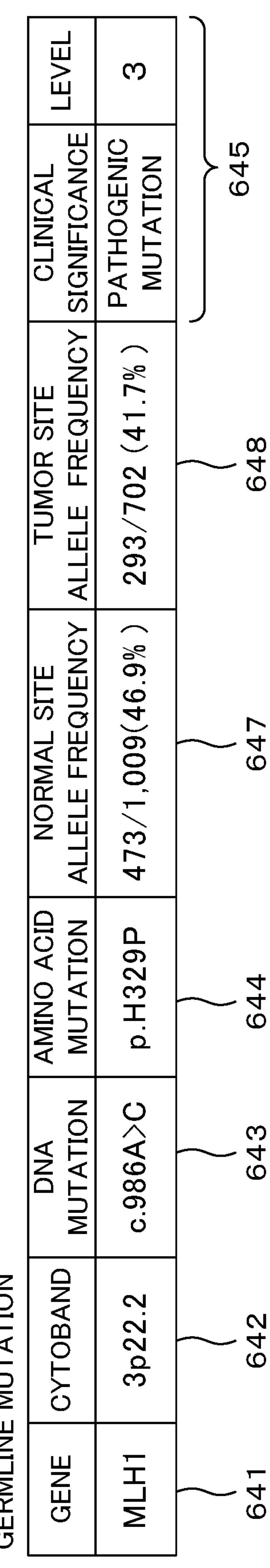
FIG. 13 is an explanatory diagram illustrating an example of a germline mutation section.

FIG. 13 is an explanatory diagram illustrating an example of the germline mutation section 64. In FIG. 13, an example of the germline mutation section 64 that is displayed on the basis of the germline mutation field in the report record exemplified in FIG. 8 is illustrated.

The germline mutation section 64 includes a gene section 641, a cytoband section 642, a DNA mutation section 643, an amino acid mutation section 644, a normal site allele frequency section 647, a tumor site allele frequency section 648, and a knowledge data section 645. In each of the gene section 641, the DNA mutation section 643, and the knowledge data section 645, the information recorded in the germline mutation field is displayed.

In the cytoband section 642, the position of the gene on the chromosome is displayed. In the amino acid mutation section 644, the mutation of the amino acid due to the DNA mutation is recorded. In the normal site allele frequency section 647, for example, an allele frequency of the normal site recorded in the file in the BAM format or the SAM format is displayed. In the tumor site allele frequency section 648, for example, an allele frequency of the tumor site recorded in the file in the BAM format or the SAM format is displayed.

FIG. 14 is an explanatory diagram illustrating an example of the analysis section 65. The analysis section 65 includes an estimation tumor content section 651 and a 652. In the estimation tumor content section 651, an estimation tumor content on the basis of the output of the learning model 53 is displayed.

In the mutation frequency correlation coefficient section 652, a correlation coefficient between a genetic mutation frequency in the specimen sampled from the normal site and a genetic mutation frequency in the specimen sampled from the tumor site is displayed. In a case where the correlation coefficient is high, the same base is often mutated in a normal site and an abnormal site, and it is determined that the specimens are derived from the same patient. In a case where the correlation coefficient is lower than a threshold value, it is suspected that the specimens are mixed up or contaminated.

The mutation frequency correlation coefficient section 652 may not be displayed. For example, in the case of performing the analysis without using the normal site specimen, the mutation frequency correlation coefficient section 652 is not required.

In a case where a user selects each section described using FIG. 10 to FIG. 14, for example, by a right click or the like, the control unit 21 displays the information recorded in the basis information field of the report record. The control unit 21 may display a link to the basis information, on the basis of the display basis information field, or may display the basis information itself. The user is capable of checking the reliability of the report by browsing the basis described in the report 60.

In the report 60, a contact name of the molecular tumor board who has reviewed the report, and the like may be displayed. The user is capable of asking a question to the molecular tumor board or consulting with the molecular tumor board, on the basis of the report 60.

The report may include information such as preprocessing performed with respect to the specimen, the number of reads of the base sequence by the reader 31, or a mapping depth to the reference sequence. A clinician knowledgeable about the genetic test is capable of determining the reliability of the report, on the basis of the information described above.

Figure 15:
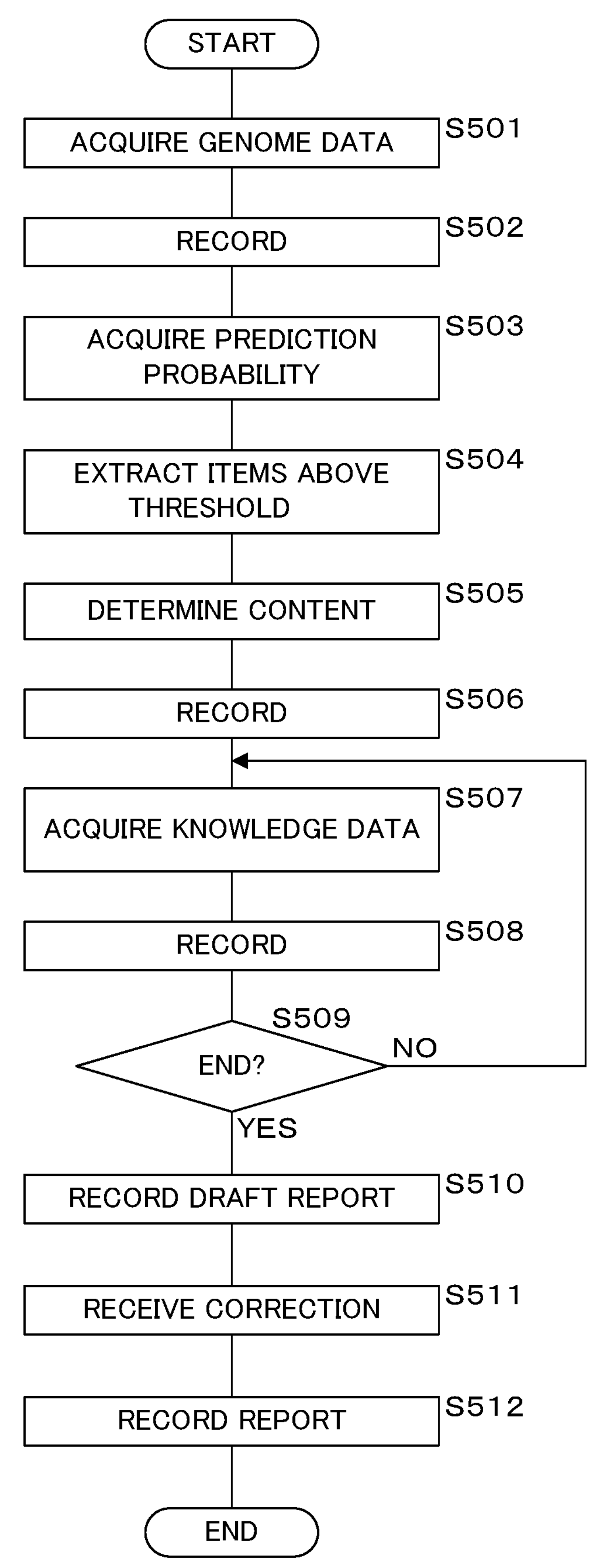
FIG. 15 is a flowchart illustrating a flow of processing of a program.

FIG. 15 is a flowchart illustrating the flow of the processing of the program. The control unit 21 acquires the genome data from the data server 32, on the basis of a report creating request (step S501). The control unit 21 add a new record in the draft report DB 55, and records data in each of the specimen ID field, the specimen field, and the genome data field (step S502).

The control unit 21 inputs the acquired genome data to the learning model 53, and acquires a prediction probability of each node of the output layer 533 (step S503). The control unit 21 extracts a genetic mutation of which the probability of a predetermined threshold value or higher is output from a node according to the genetic mutation in the output layer 533 (step S504). The threshold value may be a value different for each genetic mutation, or may be a constant value.

The control unit 21 determines the tumor content in the specimen, on the basis of a node with the highest probability among the nodes according to the tumor content in the output layer 533 (step S505). The control unit 21 records the mutation extracted in step S504 in the non-synonymous somatic mutation field of a draft report record added in step S502 or the diagnosis data field of the germline mutation field, and records the tumor content determined in step S505 in the tumor content field (step S506).

Note that, the tumor content may be calculated by another program independent from the program illustrated in FIG. 15. In such a case, step S505 is not required.

The control unit 21 searches the integrated DB 52 by setting the region in which the specimen is sampled and the genetic mutation recorded in the draft report record as a key, and acquires the knowledge data from the knowledge data field of the extracted record (step S507). The control unit 21 records the acquired knowledge data in the report record (step S508).

The control unit 21 determines whether the processing of all the genetic mutations recorded in the draft report record is ended (step S509). In a case where it is determined that the processing is not ended (NO in step S509), the control unit 21 returns to step S507. In a case where it is determined that the processing is ended (YES in step S509), the control unit 21 creates the draft of the report 60 described using FIG. 10, on the basis of the report record, and records the draft report in the auxiliary storage device 23 or the data server 32 (step S510).

Experts who are members of the molecular tumor board review the draft of the report 60, and as necessary, corrects the draft, at a molecular tumor board conference held regularly or irregularly. The molecular tumor board conference may be performed by actually gathering the experts in one room, or may be performed by a video conference, an audio conference, or the like. The molecular tumor board conference may be performed by an electronic conference using a chat system or the like.

The molecular tumor board, as necessary, refers to the genome data in the FASTQ format, the BAM format, the VCF format, or the like. The molecular tumor board may refer to a microscope photograph captured in the pathological test, or the like. The molecular tumor board may collect information from a pathologist handling the pathological test or a clinician handling the patient.

The control unit 21 receives the correction determined in the molecular tumor board conference (step S511). The control unit 21 records the report record in which the information recorded in the draft report record is corrected in the report DB 56 (step S512). The control unit 21 records the expert ID uniquely assigned to the expert who has reviewed the draft, in the expert ID field of the report record. The control unit 21 ends the processing.

The control unit 21 may notify the clinician that the report is created using an e-mail and other arbitrary means. The control unit 21 may upload the report to the electronic health record system. In a case where the clinician logs into the genomic analysis system 10, the control unit may notify that there is a new report.

The control unit 21 may receive the designation of the data of the integrated DB 52 for writing the report 60 at the start of the program described using FIG. 15. In the case of receiving the designation of the date, the control unit 21 acquires the knowledge data by using the latest integrated DB 52 at the date designated in step S507. In step S510, the control unit 21 records the draft report based on the latest information at the designated date.

For example, in the case of verifying the adequateness of the therapeutic strategy or the like determined in the past, a date at which the medical practice is performed is designated, and the program described using FIG. 15 is executed, and thus, the draft report based on the latest information at the date can be created.

Data may be added to the training data DB 51, on the basis of the information recorded in the report DB 56, information after the medical treatment, information after medication, and the like, and the relearning of the learning model 53 may be performed. By adding data that has been reviewed by the expert to the training data, the accuracy of the learning model 53 can be improved.

According to this embodiment, it is possible to provide the learning model 53 that automatically extracts the clinically important mutation, on the basis of the base sequence read from the specimen. By using the learning model 53, even a medical doctor not having an advanced technical knowledge in the genetic test is capable of determining the presence or absence of a clinically important genetic mutation.

According to this embodiment, by using the integrated DB 52, it is possible to provide the genomic analysis system 10 that presents the medical information about the genetic mutation to the user. In the field of the genetic test, the research is rapidly performed, and new findings are frequently published, and thus, it is difficult for each medical doctor to constantly grasp the latest information. The medical information is provided, and the basis thereof is also presented, on the basis of the integrated DB 52, and thus, the medical doctor is capable of providing a suitable medical procedure to the patient, as necessary, by checking the basis.

By reviewing the molecular tumor board with the draft report and reflecting the correction of the molecular tumor board, it is possible to provide the genomic analysis system 10 that creates the report 60 with high reliability. By reviewing the draft report with the molecular tumor board, it is possible to create the report 60, on the basis of new information that is not included in the training data DB 51.

In a case where the clinician has the technical knowledge in the genetic test, the review of the molecular tumor board may be omitted, and the draft report may be directly used in the report 60. The patient or the clinician may acquire the draft report and the genome data, and may ask for feedback to a medical specialist selected by the patient or the clinician.

EMBODIMENT 2

This embodiment relates to the genomic analysis system 10 that also analyzes a base sequence of an RNA in addition to a DNA. The description of the parts common to Embodiment 1 will be omitted.

In this embodiment, the specimen sampled from the tumor site is divided into three parts. One is used in the pathological test, and another is used in the DNA analysis. In the last one, the RNA is extracted in preprocessing, the base sequence of the RNA is read by the reader 31, and analysis is performed by the same method as that of the DNA.

By analyzing the RNA, it is possible to obtain information on a gene abnormality that occurs in the tumor site. The gene abnormality that occurs in the tumor site, for example, is a fusion gene in which a plurality of DNAs are fused by translocation or gene rearrangement, or exon skipping in which a part of the DNA is dropped when the DNA is transcribed to the RNA. In the report 60 of this embodiment, for example, an RNA section 66 that displays the information obtained by analyzing the RNA is displayed between the non-synonymous somatic mutation section 63 and the germline mutation section 64.

Figure 16A:
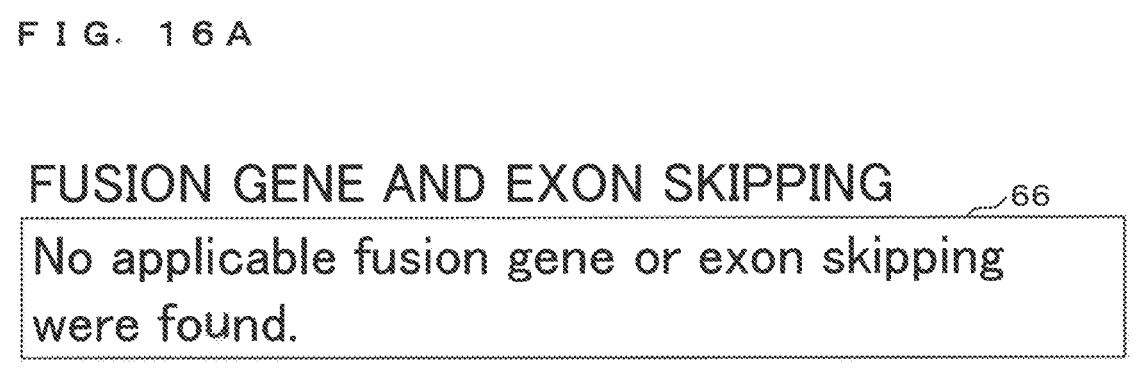
Figure 16B:
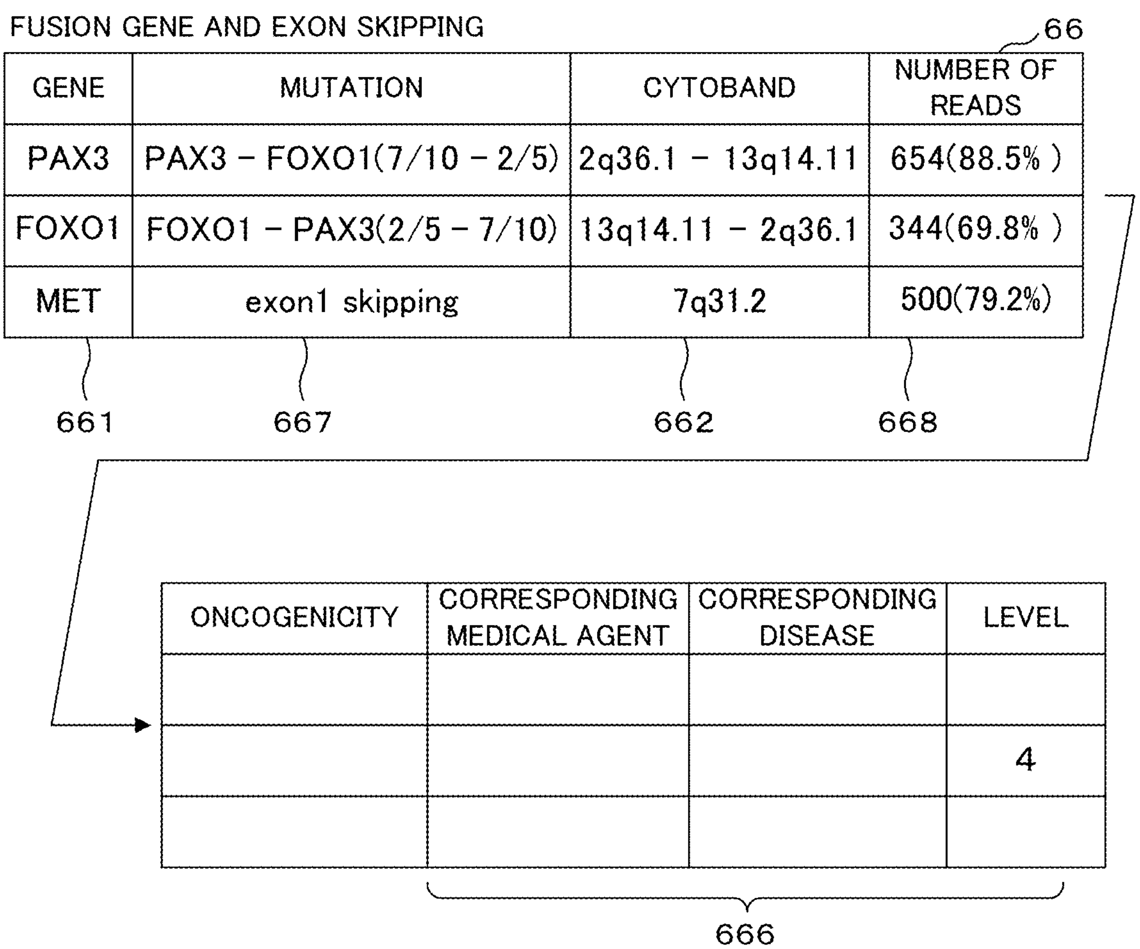
FIG. 16B is an explanatory diagram illustrating an example of the RNA section.

FIG. 16A and FIG. 16B are explanatory diagrams illustrating an example of the RNA section 66. FIG. 16A and FIG. 16B illustrate an example of the RNA sections 66 that are displayed in reports different from each other, respectively. FIG. 16A illustrates an example of the RNA section 66 for a specimen in which an abnormality is not found in an RNA. FIG. 16B illustrates an example of the RNA section 66 for a specimen in which a fusion gene and exon skipping are found.

The RNA section 66 illustrated in FIG. 16B includes a gene section 661, a mutation section 667, a cytoband section 662, a number of reads section 668, and a knowledge data section 666. In the gene section 661, a gene of a transcription source from which the RNA is transcribed is displayed.

In the mutation section 667, the mutation of the RNA is displayed. For example, in the top row of FIG. 16B, the detection of a fusion gene of a PAX3 gene and a FOXO1 gene is displayed. In the bottom row of FIG. 16B, the detection of exon 1 skipping of a MET gene is displayed.

In the cytoband section 662, the position of a gene on a chromosome is displayed. In the number of reads section 668, the number and the ratio of reads in which the mutation is detected among the reads read by the reader 31 are displayed. The information displayed in the number of reads section 668 is read from the file in the FASTQ format. In the knowledge data section 666, the information acquired from the integrated DB 52 is displayed.

According to this embodiment, it is possible to provide the genomic analysis system 10 that detects the gene abnormality that occurs in the tumor and displays the gene abnormality in the report 60.

EMBODIMENT 3

This embodiment relates to the genomic analysis system 10 that outputs an additional report indicating a change in the report 60 output in the past in a case where the integrated DB 52 is updated. The description of the parts common to Embodiment 1 will be omitted.

FIG. 17 is an explanatory diagram illustrating a record layout of a change history DB. The change history DB is a DB in which the genetic mutation recorded in the integrated DB 52, and a change date at which the knowledge data is changed are recorded in association with each other. The change history DB includes a genome mutation field and a change date field.

The genome mutation field includes a tumor site specimen field, a gene field, and a mutation contents field. The change date field includes an arbitrary number of subfields such as a first change date field and a second change date field. The change history DB includes one record for one medical information piece recorded in the integrated DB 52.

In the tumor site specimen field, the region in which the specimen is sampled is recorded. In the gene field, the gene in which the mutation is detected is recorded. Note that, in the record in which the medical information about the combination of the plurality of mutations is recorded, the plurality of genes are recorded in the gene field.

In the first change date field, a date at which a record for the genetic mutation recorded in the genome mutation field is recorded in the integrated DB 52 is recorded. In the second change date field and the subsequence, a date at which the medical information recorded in the integrated DB 52 is changed is recorded.

FIG. 18 is an explanatory diagram illustrating a record layout of the report DB 56 of Embodiment 3. In the report DB 56 of this embodiment, a check date field is added to the report DB 56 of Embodiment 1 described using FIG. 8. In the check date field, a date at which an update status of the integrated DB 52 is checked is recorded.

Figure 19:
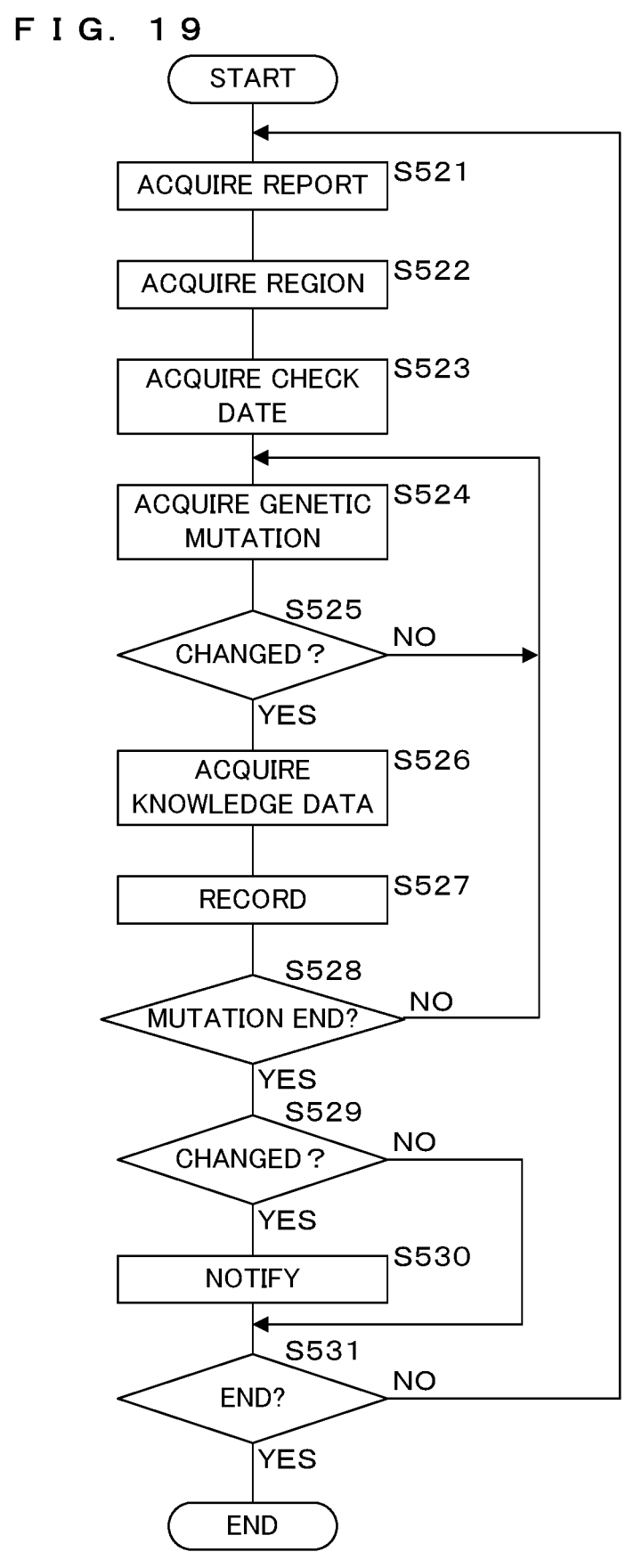

FIG. 19 is a flowchart illustrating the flow of the processing of a program that outputs the additional report. The control unit 21 acquires the report record recorded in the report DB 56 (step S521). The control unit 21 acquires the region in which the specimen is sampled, which is recorded in the normal site specimen field and the tumor site specimen field (step S522). The control unit 21 acquires the check date recorded in the check date field (step S523).

The control unit 21 acquires the genetic mutation recorded in the gene field of the non-synonymous somatic mutation field or the germline mutation field (step S524). The control unit 21 searches the change history DB by setting the region in which the specimen is sampled, which is acquired in step S522, and the genetic mutation acquired in step S524, as a key, and extracts a record. The control unit 21 compares a date at which the extracted record is recorded in the change date field with the check date acquired in step S523, and determines whether the knowledge data is changed after the check date (step S525).

In a case where it is determined that the knowledge data is not changed (NO in step S525), the control unit 21 returns to step S524. In a case where it is determined that the knowledge data is changed (YES in step S525), the control unit 21 searches the latest integrated DB 52 by setting the region in which the specimen is sampled, which is acquired in step S522, and the genetic mutation acquired in step S524, as a key, and extracts a record. The control unit 21 acquires the knowledge data from the extracted record (step S526).

The control unit 21 records the knowledge data acquired in step S526 in the knowledge data field of the report record (step S527). The control unit 21 may create the copy of the report record, and may record the knowledge data acquired in step S526.

The control unit 21 determines whether the processing of all the mutations recorded in the report record acquired in step S521 is ended (step S528). In a case where it is determined that the processing is not ended (NO in step S528), the control unit 21 returns to step S524.

In a case where it is determined that the processing is ended (YES in step S528), the control unit 21 determines whether there is a genetic mutation in which a change in the knowledge data is determined in step S525 (step S529). In a case where it is determined that there is the genetic mutation (YES in step S529), the control unit 21 notifies the clinician that the report is changed (step S530). The notification, for example, can be performed by arbitrary means such as an e-mail or a messenger.

The control unit 21 may perform notification with respect to the molecular tumor board in step S530, may receive the correction based on a review result, and then, may perform notification with respect to the clinician or the hospital. In a case where it is determined that there is no genetic mutation in which a change in the knowledge data is determined (NO in step S529) or after the end of step S530, the control unit 21 determines whether the processing is ended (step S531).

In a case where it is determined that the processing is not ended (NO in step S531), the control unit 21 returns to step S521. In a case where it is determined that the processing is ended (YES in step S531), the control unit 21 ends the processing.

According to this embodiment, it is possible to provide the genomic analysis system 10 that outputs the additional report in a case where new medical information about the report created in the past is published. The clinician is capable of receiving additional information about a medical agent, a therapeutic trial, a therapeutic method, or the like that can be expected to be effective on the patient under the medical treatment, and reflecting the additional information on the therapeutic strategy.

The control unit 21 may receive the designation of the report 60 that does not require the additional information. The clinician is capable of designating that an additional report is not required for the report 60 for the patient who has completed the medical treatment, or the like. In step S521, the control unit 21 excludes the report that does not require the additional information from an acquisition target, and thus, avoids the writing of the additional report that is not required.

EMBODIMENT 4

This embodiment relates to the genomic analysis system 10 that provides an incentive to the expert participating in the molecular tumor board. The description of the parts common to Embodiment 1 will be omitted.

FIG. 20 is an explanatory diagram illustrating a record layout of an expert DB. The expert DB is a DB in which an expert ID uniquely assigned to the expert participating in the molecular tumor board, a specialty area, and a point are recorded in association with each other.

The expert DB includes an expert ID field, a specialty area field, and a point field. In the expert ID field, the expert ID is recorded. In the specialty area field, the specialty area of the expert is recorded. In the point field, a point provided to the expert is recorded.

The expert is capable of gaining the point whenever participating in the molecular tumor board and reviewing the draft report. The expert is capable of exchanging the accumulated points, for example, for a cash voucher, a report writing request voucher that can be used when requesting the writing of the report 60, a learning model voucher that can be used when requesting gene analysis using the learning model 53, or the like. According to the point, it is possible to provide the incentive for the participation in the molecular tumor board to the expert.

The point, for example, may be set such that 5 points are provided for one review. For example, a leader of the molecular tumor board may determine the point to be provided to each expert, on the basis of the amount of statement or the contents of a comment when the expert reviews the draft report. The point to be provided for one review may be set on the basis of a participation frequency in the molecular tumor board.

FIG. 21 is an explanatory diagram illustrating an example of a screen for selecting a participant in the molecular tumor board. The screen illustrated in FIG. 21 is displayed on an information device such as a personal computer, a tablet, or a smart phone that is used by a person in charge of the secretariat of the molecular tumor board. The information device that is used by the person in charge of the secretariat is connected to the information processing device 20 through a network.

The screen for selecting the participant in the molecular tumor board includes a specimen information section 74, a narrowing condition section 75, a re-search button 76, a candidate list 77, a check button 78, and a request transmission button 79. In the specimen information section 74, the information about the specimen that is reviewed by the molecular tumor board is displayed.

In the narrowing condition section 75, items that are used when narrowing the experts are displayed. The user is capable of selecting a narrowing condition by selecting a checkbox displayed at the head of each item. Note that, the narrowing condition section 75 may include a section for receiving a free keyword. In the candidate list 77, a candidate list of the expert participating in the molecular tumor board is displayed.

The user sets a desired condition using the narrowing condition section 75, and selects the re-search button 76. The set condition is transmitted to the information processing device 20. The control unit 21 extracts an expert who meets the set condition, and transmits the expert to an information device used by the user.

In the candidate list 77, a list of the experts who meet the set condition is displayed. The user selects the expert requesting the participation in the molecular tumor board using a checkbox displayed on the right end of the candidate list 77.

In a case where the number of experts displayed in the candidate list 77 is excessively large or small, the user suitably changes the setting of the narrowing condition section 75, and performs re-search. In a case where the user selects the check button 78, a list of the selected experts is displayed. In a case where the user selects the request transmission button 79, the list of the selected experts is transmitted to the information processing device 20.

The control unit 21 stores the specimen ID and the expert ID of the selected expert in the auxiliary storage device 23 in association with each other. The control unit 21 transmits an e-mail in which a uniform resource locator (URL) is described to each expert.

FIG. 22 is an explanatory diagram illustrating an example of a screen for checking a participation request for the molecular tumor board. FIG. 22 is a screen that is displayed on an information device used by the expert in a case where the expert accesses a website indicated by the URL.

The screen for checking the participation request for the molecular tumor board includes a request list 72 and a participation button 71. In the request list 72, a list of molecular tumor boards requesting the expert to participate is displayed. For each molecular tumor board, information such as the region where the specimen is sampled, the patient information, and medical institutions requesting the writing of the report 60 is displayed.

The expert selects the participation button 71 for the molecular tumor board in which the expert desires to participate by the request list 72. The control unit 21 sets an electronic conference room in which the expert who has selected the participation button 71 participates, and uploads the draft report. The participant reviews the report on the electronic conference room. A leader designated in advance draws a conclusion, and ends the electronic conference room. Note that, since an electronic conference system has been widely used from the related art, the detailed description of the processing of the control unit 21 will be omitted.

After the electronic conference room is ended, the control unit 21 provides a point to the expert who has participated in the molecular tumor board. Specifically, the control unit 21 extracts a record according to the expert who has participated in the molecular tumor board from the expert DB, and adds the point to the point field.

Figure 23:
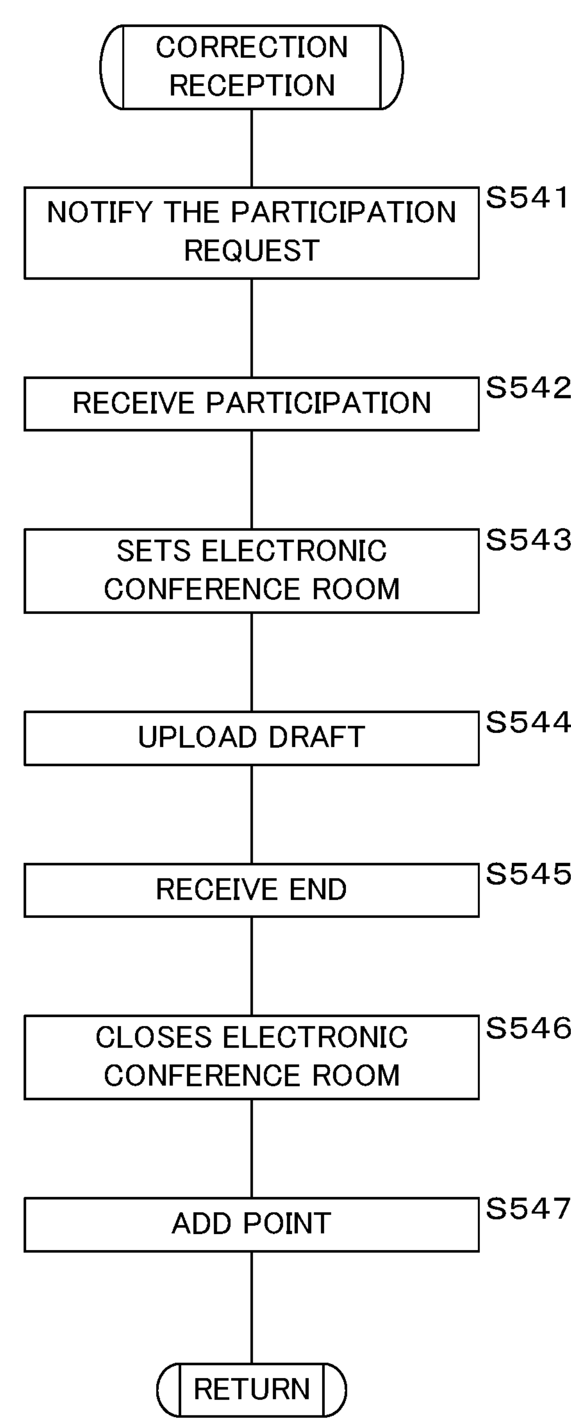
FIG. 23 is a flowchart illustrating a flow of processing of a correction reception subroutine of Embodiment 4.

FIG. 23 is a flowchart illustrating the flow of the processing of a correction reception subroutine of Embodiment 4. The correction reception subroutine is a subroutine in which the participation of the expert in the molecular tumor board is received, and the point is provided to the expert who has participated. The correction reception subroutine is activated instead of step S511 of the program of Embodiment 1 described using FIG. 15.

The control unit 21 prepares an molecular tumor board participation request the screen described using FIG. 22 for each expert registered in the expert DB, transmits the e-mail in which the URL is described, and notifies the participation request (step S541). The e-mail transmitted to the expert is a review request for updating the integrated DB.

The control unit 21 is capable of setting which expert is requested to review the draft report, on the basis of the specialty area recorded in the specialty area field of the expert DB. For example, the control unit 21 notifies the participation request to the expert in which respiratory is registered in the specialty area field, for the molecular tumor board regarding to a case in which the the tumor site specimen was sampled from respiratory system, and a case in which requested by the respiratory department.

The control unit 21 may select the expert registered in the expert DB for each category, and may notify the participation request. The control unit 21 may notify the participation request to all the experts registered in the expert DB. The control unit 21 receives the selection of the participation button 71 by the expert, and thus, receives the participation in the molecular tumor board (step S542). The control unit 21 sets the electronic conference room in which the participant for each molecular tumor board is registered (step S543). The control unit 21 transmits access information for the electronic conference room to each participant.

The control unit 21 uploads the draft report to the electronic conference room such that the participant is capable of browsing the draft report (step S544). The participant performs communication with other participants through the electronic conference room, and reviews the draft report.

The leader designated in advance draws a conclusion, and performs a manipulation of ending the electronic conference room. The control unit 21 receives the end manipulation (step S545). The control unit 21 closes the electronic conference room (step S546). The control unit 21 extracts the record according to the expert who has participated in the molecular tumor board from the expert DB, and adds the point to the point field (step S547). The control unit 21 ends the processing.

According to this embodiment, it is possible to provide the genomic analysis system 10 that provides the incentive to the participation in the molecular tumor board. By distributing a profit obtained by a fee for using the learning model, a fee for writing the report, and the like to the expert as the point, it is possible to provide genomic analysis system 10 that easily ensures the expert who participates in the molecular tumor board.

Whether to participate in each molecular tumor board can be determined by the expert oneself, and thus, it is possible to provide the genomic analysis system 10 that gathers highly motivated participants. Since the expert review is performed by using the electronic conference room, it is possible to provide the genomic analysis system 10 in which even a busy expert easily participates in the molecular tumor board.

EMBODIMENT 5

This embodiment relates to the genomic analysis system 10 that requests the expert to review the information recorded in the integrated DB 52. The description of the parts common to Embodiment 4 will be omitted.

FIG. 24 is an explanatory diagram illustrating an example of an integrated DB review participation request screen. The control unit 21 transmits the e-mail in which the URL is described to each expert. In a case where the expert accesses the website indicated by the URL by using the information device such as a personal computer or a smart phone, the integrated DB review participation request screen illustrated in FIG. 24 is displayed on the information device.

The integrated DB review participation request screen includes a request list 73 and a participation button 71. In the request list 73, a list of the medical information that is requested to be reviewed by the expert is displayed. For each medical information piece, the gene, the DNA mutation, and the information source of a target are displayed. The target of the integrated DB review may be information that is not associated with a specific genetic mutation, as exemplified in No. 3 of FIG. 24.

The expert is capable of determining whether the information is medical information about a medical agent, a disease, or a therapeutic trial that is a specialized area of the expert by the request list 73. In a case where the expert desires to participate in the review, the expert selects the participation button 71. The control unit 21 sets the electronic conference room in which the expert who has selected the participation button 71 participates, and uploads the draft report. The participant reviews the report on the electronic conference room. The leader designated in advance draws a conclusion, and ends the electronic conference room.

Note that, the review may be performed by one expert alone. In this case, the electronic conference room may not be used.

The control unit 21 executes the addition of a new record to the integrated DB 52 or the update of the existing record, on the basis of the review result.

Figure 25:
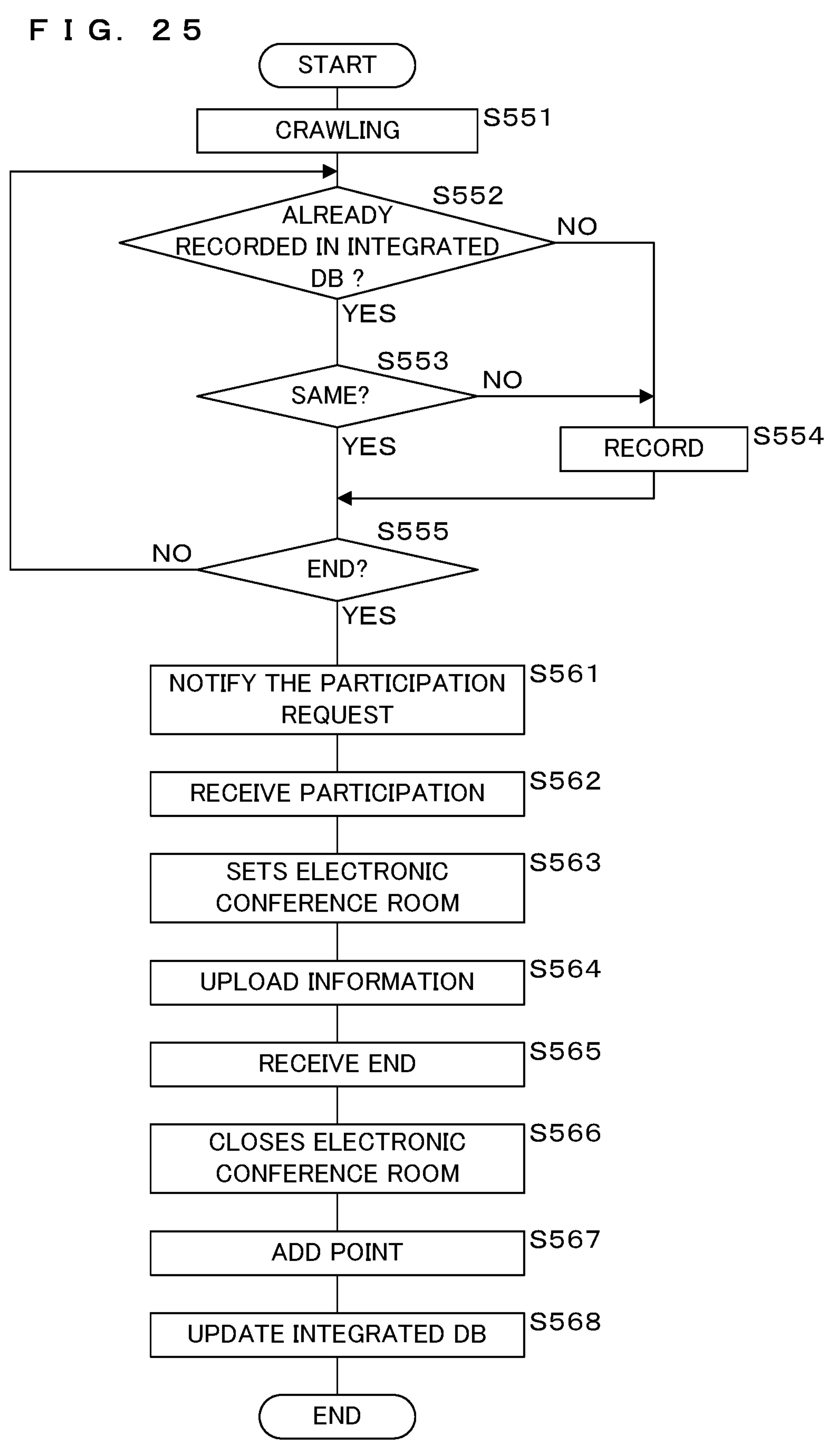
FIG. 25 is a flowchart illustrating a flow of processing of a program that updates an integrated DB 52.

FIG. 25 is a flowchart illustrating the flow of the processing of a program that updates the integrated DB 52. In the following description, a case in which the information processing device 20 updates the integrated DB 52 will be described as an example. The update of the integrated DB 52 may be executed by an information device other than the information processing device 20.

The control unit 21 performs crawling of patrolling various medical information DBs 58, collecting new medical information about the genetic mutation, and compiling a database (step S551). The crawling is executed by a program referred to as a crawler or a robot. Since the crawling has been widely used from the related art, the detailed description thereof will be omitted.

The control unit 21 selects the medical information collected by the crawling, and determines whether the information is the information about the genetic mutation that is already recorded in the integrated DB 52 (step S552). In a case where it is determined that the information is the information about the genetic mutation that is recorded in the integrated DB 52 (YES in step S552), the control unit 21 determines whether the contents are the same as those of the information that is recorded in the integrated DB 52 (step S553).

In a case where it is determined that the information is not the information about the genetic mutation that is recorded in the integrated DB 52 (NO in step S552), or in a case where it is determined that the contents are not the same as those of the information that is recorded in the integrated DB 52 (NO in step S553), the control unit 21 records that the medical information under the processing is a review target (step S554).

In a case where it is determined that the contents are the same (YES in step S553), or after the end of step S554, the control unit 21 determines whether the processing of the medical information collected in step S551 is ended (step S555). In a case where it is determined that the processing is not ended (NO in step S555), the control unit 21 returns to step S552.

In a case where it is determined that the processing is ended (YES in step S555), the control unit 21 prepares the integrated DB review participation request screen described using FIG. 24 for each expert registered in the expert DB, transmits the e-mail in which the URL is described, and notifies the participation request (step S561).

The control unit 21 receives the selection of the participation button 71 by the expert, and thus, receives the participation in the review (step S562). The control unit 21 sets the electronic conference room in which the participant for each review is registered (step S563). The control unit 21 transmits the access information for the electronic conference room to each participant.

The control unit 21 uploads the medical information collected by the crawling to the electronic conference room such that the participant is capable of browsing the medical information (step S564). The participant performs communication with other participants through the electronic conference room, and reviews the medical information.

The leader designated in advance draws a conclusion, and performs the manipulation of ending the electronic conference room. The conclusion may be determined by majority voting of the experts who participate. The control unit 21 receives the end manipulation (step S565). The control unit 21 closes the electronic conference room (step S566). The control unit 21 extracts the record according to the expert who has participated in the review from the expert DB, and adds the point to the point field (step S567). The control unit 21 updates the integrated DB 52, on the basis of a review result about each medical information piece (step S568). The control unit 21 ends the processing.

According to this embodiment, it is possible to provide the genomic analysis system 10 that automatically collects the information registered in the integrated DB 52 by the crawling, and then, updates the integrated DB 52 through the review of the expert. By utilizing a crawling technology, it is possible to provide the genomic analysis system 10 that suitably reflects new medical information on the integrated DB 52.

By implementing the review of the expert before registering the collected medical information in the integrated DB 52, it is possible to provide the genomic analysis system 10 that maintains the reliability of the integrated DB 52, and outputs the accurate report 60.

By distributing the profit obtained by the fee for using the learning model, the fee for writing the report writing fee, and the like to the expert as the point, it is possible to provide the genomic analysis system 10 that easily ensures the expert who participates in the review.

Whether to participate in each review can be determined by the expert oneself, and thus, it is possible to provide the genomic analysis system 10 that gathers highly motivated review participants. Since the review is performed by using the electronic conference room, it is possible to provide the genomic analysis system 10 in which even a busy expert easily participates in the review.

EMBODIMENT 6

Figure 26:
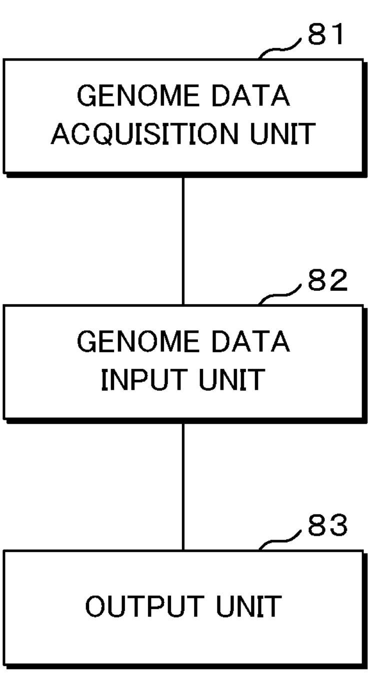
FIG. 26 is a function block diagram of an information processing device when predicting a clinically significant genetic mutation from the genome data.

FIG. 26 is a function block diagram of the information processing device 20 when predicting a clinically significant genetic mutation from the genome data. The information processing device 20 includes a genome data acquisition unit 81, a genome data input unit 82, and an output unit 83.

The genome data acquisition unit 81 acquires the genome data obtained by reading the base sequence included in the specimen. The genome data input unit 82 receives the genome data, and inputs the genome data acquired by the genome data acquisition unit 81 to the learning model 53 that outputs the prediction of the genetic mutation. The output unit 83 outputs the prediction output from the learning model 53, on the basis of the genome data input by the genome data input unit 82.

Figure 27:
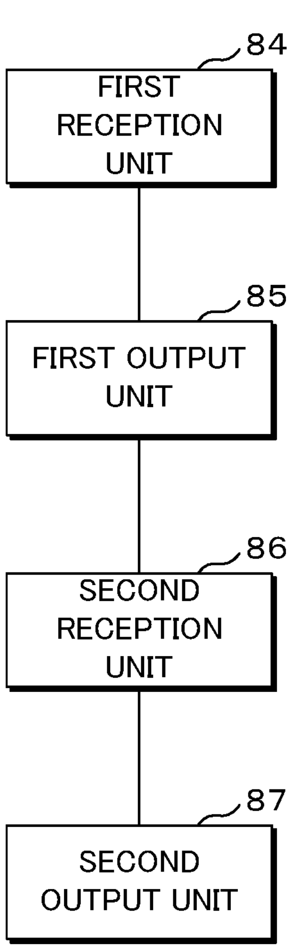
FIG. 27 is a function block diagram of the information processing device when writing a report, on the basis of the genetic mutation and the integrated DB 52.

FIG. 27 is a function block diagram of the information processing device 20 when writing the report, on the basis of the genetic mutation and the integrated DB 52. The information processing device 20 includes a first reception unit 84, a first output unit 85, a second reception unit 86, and a second output unit 87.

The first reception unit 84 receives the genetic mutation detected from the specimen. The first output unit 85 outputs the report in which an analysis result of the specimen and the version of the integrated DB 52 are recorded in association with each other, on the basis of the genetic mutation received from the first reception unit 84, and the integrated DB 52 in which the medical information relevant to the genetic mutation acquired from the plurality of information sources, and an acquisition date and basis information of the medical information are integrated in association with each other.

The second reception unit 86 receives a date in the past, a report output request at the date, and the genetic mutation detected from the specimen. The second output unit 87 outputs the report in which the analysis result of the specimen and the version of the integrated DB 52 are recorded in association with each other, on the basis of the genetic mutation received from the second reception unit 86, and the integrated DB 52 at the date.

EMBODIMENT 7

Figure 28:
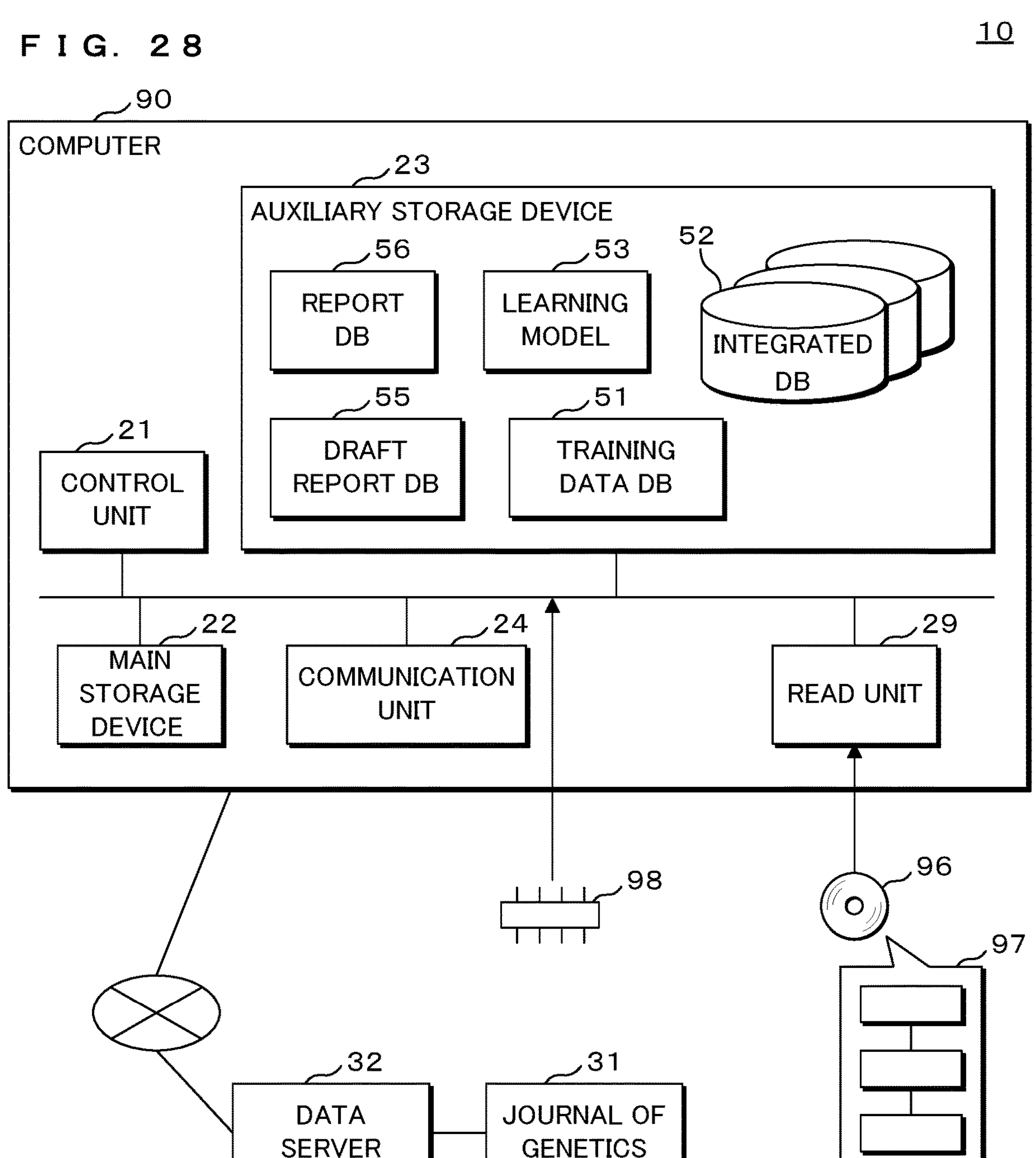
FIG. 28 is an explanatory diagram illustrating a configuration of a genomic analysis system of Embodiment 7.

This embodiment relates to an aspect in which the genomic analysis system 10 of this embodiment is attained by operating a general-purpose computer 90 and a program 97 in combination. FIG. 28 is an explanatory diagram illustrating the configuration of the genomic analysis system 10 of Embodiment 7. The description of the parts common to Embodiment 1 will be omitted.

The genomic analysis system 10 of this embodiment includes the computer 90, the reader 31, and the data server 32.

The computer 90 includes the control unit 21, the main storage device 22, the auxiliary storage device 23, the communication unit 24, a read unit 29, and the bus. The computer 90 is an information device such as a general-purpose personal computer, a tablet, or a server computer.

The program 97 is recorded in a portable recording medium 96. The portable recording medium 96 is an example of a non-transitory computer readable medium including program 97. The control unit 21 reads the program 97 through the read unit 29, and stores the program in the auxiliary storage device 23. In addition, the control unit 21 may read out the program 97 stored in a semiconductor memory 98 such as a flash memory that is mounted on the computer 90. Further, the control unit 21 may download the program 97 from other server computers not illustrated, which are connected through the communication unit 24 and a network not illustrated, and may store the program in the auxiliary storage device 23.

The program 97 is installed as a control program of the computer 90, is loaded in the main storage device 22, and is executed. Accordingly, the computer 90 functions as the information processing device 20 described above.

The technical features (constituents) described in each example can be combined with each other, and a new technical feature can be formed by the combination.

The embodiments disclosed herein are an exemplification in all respects, and are not to be considered restrictive. The scope of the present invention is indicated by the claims but not the meaning described above, and is intended to include all changes within the meaning and the range equivalent to the claims.

It is to be noted that, as used herein and in the appended claims, the singular forms "a", "an", and "the" include plural referents unless the context clearly dictates otherwise.

DESCRIPTION OF REFERENCE NUMERALS

10 Genomic analysis system
20 Information processing device
21 Control unit (processor)
22 Main storage device
23 Auxiliary storage device
24 Communication unit
29 Read unit
31 Reader
32 Data server
51 Training data DB
52 Integrated DB
53 Learning model
531 Input layer
532 Intermediate layer
533 Output layer
55 Draft report DB
56 Report DB
58 Medical information DB
60 Report
61 Bibliographic item section
611 ID section
612 Patient information section
613 Specimen section
614 Pathological tissue diagnosis section
615 Specimen number section
62 Comment section
63 Non-synonymous somatic mutation section
631 Gene section
632 Cytoband section
633 DNA mutation section
634 Amino acid mutation section
635 Allele frequency section
636 Knowledge data section
64 Germline mutation section
641 Gene section
642 Cytoband section
643 DNA mutation section
644 Amino acid mutation section
645 Knowledge data section
647 Normal site allele frequency section
648 Tumor site allele frequency section
65 Analysis section
651 Estimation tumor content section
652 Mutation frequency correlation coefficient section
66 RNA section
661 Gene section
662 Cytoband section
666 Knowledge data section
667 Mutation section
668 Number of reads section
71 Participation button
72 Request list
73 Request list
74 Test body information section
75 Narrowing condition section
76 Re-search button
77 Candidate list
78 Check button
79 Request transmission button
81 Genome data acquisition unit
82 Genome data input unit
83 Output unit
84 First reception unit
85 First output unit
86 Second reception unit
87 Second output unit
90 Computer
96 Portable recording medium (non-transitory computer readable medium)
97 Program
98 Semiconductor memory

The invention claimed is:

1. A non-transitory computer readable medium including program instructions which when executed by a processor causing a computer to execute a process comprising:

acquiring, by the processor, training data in which tumor site genome data obtained by reading a base sequence included in a specimen collected from a tumor site of a patient, normal site genome data, and a genetic mutation concerning the patient are recorded in association with each other, for a plurality of genetic tests performed in the past; and generating, by the processor, a learning model for outputting a prediction of the genetic mutation concerning the patient in a case where the tumor site genome data obtained by reading the base sequence included in the specimen collected from the tumor site of the patient and the normal site genome data are input, by setting the tumor site genome data and the normal site genome data as input and the genetic mutation as output.

2. The non-transitory computer readable medium according to claim 1, wherein the learning model outputs a predicted position of a mutated base.

3. The non-transitory computer readable medium according to claim 1, wherein the learning model outputs a prediction of a tumor content in the specimen collected from the tumor site.

4. A non-transitory computer readable medium including program instructions which when executed by a processor causing a computer to execute a process comprising:

acquiring, by the processor, tumor site genome data obtained by reading a base sequence included in a specimen collected from a tumor site of a patient and normal site genome data;

inputting, by the processor, the acquired tumor site genome data and the normal site genome data to a learning model that outputs a prediction of a genetic mutation concerning the patient upon input of tumor site genome data obtained by reading a base sequence included in a specimen collected from the tumor site of the patient and the normal site genome data; and outputting, by the processor, the prediction of a genetic mutation output from the learning model.

5. A non-transitory computer readable medium including program instructions which when executed by a processor causing a computer to execute a process comprising:

outputting, by the processor, in a case where a report output request is received, a report in which an analysis result of a genetic mutation concerning a patient and a version of an integrated database (DB) are recorded in association with each other, on the basis of a prediction of a genetic mutation output from a learning model upon inputting tumor site genome data obtained by reading a base sequence included in a specimen collected from a tumor site of the patient and normal site genome data, the learning model outputting a prediction of a genetic mutation concerning the patient upon input of tumor site genome data obtained by reading the base sequence include in the specimen collected from the tumor site of the patient and the normal site genome data, and the integrated DB in which medical information about the genetic mutation acquired from a plurality of information sources, and an acquisition date and basis information of the medical information are integrated in association with each other; and outputting, by the processor, in a case where a past date and the report output request at the past date are received, the report in which the analysis result of the genetic mutation concerning the patient and the version of the integrated DB are recorded in association with each other, on the basis of the prediction and the integrated DB at the past date.

6. The non-transitory computer readable medium according to claim 5, wherein the report includes medical information extracted from the integrated DB by setting the prediction of the genetic mutation detected as a key.

7. The non-transitory computer readable medium according to claim 6, wherein, in a case where the integrated DB is updated by adding the medical information about the genetic mutation, an additional report is output on the basis of the prediction of the genetic mutation and the updated integrated DB.

8. The non-transitory computer readable medium according to claim 7, wherein a review request for updating the integrated DB is transmitted to an expert, a review result with respect to the transmitted review request is received, and an incentive with respect to the received review result is recorded in association with the expert.

9. The non-transitory computer readable medium according to claim 5, wherein, in a case where the integrated DB is updated by adding the medical information about the genetic mutation, an additional report is output on the basis of the prediction of the genetic mutation and the updated integrated DB.

10. The non-transitory computer readable medium according to claim 9, wherein a review request for updating the integrated DB is transmitted to an expert, a review result with respect to the transmitted review request is received, and an incentive with respect to the received review result is recorded in association with the expert.

11. The non-transitory computer readable medium according to claim 5, wherein a review request for the report is transmitted to an expert, a review result with respect to the transmitted review request is received, and an incentive with respect to the received review result is recorded in association with the expert.

12. The non-transitory computer readable medium according to claim 11, wherein the incentive varies on the basis of the review result.

13. A non-transitory computer readable medium including program instructions which when executed by a processor causing a computer to execute a process comprising:

acquiring, by the processor, tumor site genome data obtained by reading a base sequence included in a specimen collected from a tumor site of a patient and normal site genome data, inputting, by the processor, the acquired tumor site genome data and the normal site genome data to a learning model that outputs a prediction of a genetic mutation concerning a patient upon input of tumor site genome data obtained by reading a base sequence included in the specimen collected from the tumor site of the patient and the normal site genome data;

acquiring, by the processor, the prediction of the genetic mutation output from the learning model, on the basis of the input tumor site genome data and the normal site genome data; and outputting, by the processor, a report in which an analysis result of the specimen and a version of an integrated DB are recorded in association with each other, on the basis of the acquired prediction, and the integrated DB in which medical information about the genetic mutation acquired from a plurality of information sources, and an acquisition date and basis information of the medical information are integrated in association with each other.

14. The non-transitory computer readable medium according to claim 13, wherein a review request for the report is transmitted to an expert, a review result with respect to the transmitted review request is received, and an incentive with respect to the received review result is recorded in association with the expert.

15. The non-transitory computer readable medium according to claim 14, wherein the incentive is a cash voucher, a report writing request voucher, or a learning model voucher.

16. The non-transitory computer readable medium according to claim 14, wherein the incentive varies on the basis of the review result.

17. An information processing device comprising:

a processor executing program code to perform:

receiving, by the processor, a prediction of a genetic mutation output from a learning model upon inputting tumor site genome data obtained by reading a base sequence included in a specimen collected from a tumor site of a patient and normal site genome data, the learning model outputting a prediction of a genetic mutation concerning the patient upon input of tumor site genome data obtained by reading a base sequence included in the specimen collected from the tumor site of the patient and the normal site genome data;

outputting, by the processor, a report in which an analysis result of the genetic mutation concerning the patent and a version of an integrated DB are recorded in association with each other, on the basis of the received prediction of a genetic mutation and the integrated DB in which medical information about the genetic mutation acquired from a plurality of information sources, and an acquisition date and basis information of the medical information are integrated in association with each other;

receiving, by the processor, a past date, a report output request at the past date, and the prediction; and outputting, by the processor, the report in which the analysis result of the genetic mutation of the patient and the version of the integrated DB are recorded in association with each other, on the basis of the prediction and the integrated DB at the past date.

18. An information processing device comprising:

a processor executing program code to perform:

acquiring, by the processor, tumor site genome data obtained by reading a base sequence included in a specimen collected from a tumor site of a patient and normal site genome data;

inputting, by the processor, the acquired tumor site genome data and the normal site genome data to a learning model that outputs a prediction of a genetic mutation concerning the patient upon input of tumor site genome data obtained by reading a base sequence included in a specimen collected from the tumor site of the patient and the normal site genome data; and outputting, by the processor, the prediction of a genetic mutation output from the learning model.

19. An information processing method for causing a processor of an information processing apparatus to perform processing for:

acquiring, by the processor, tumor site genome data obtained by reading a base sequence included in a specimen collected from a tumor site of a patient and normal site genome data;

inputting, by the processor, the acquired tumor site genome and the normal site genome data to a learning model that outputs a prediction of a genetic mutation concerning the patient upon input of tumor site genome data obtained by reading a base sequence included in the specimen collected from the tumor site of the patient and the normal site genome data; and outputting, by the processor, the prediction of the genetic mutation concerning the patient output from the learning model.

20. A method for generating a learning model for causing a processor of a computer to execute processing of:

acquiring, by the processor, training data in which tumor site genome data obtained by reading a base sequence included in a specimen collected from a tumor site of a patient and normal site genome data are recorded in association with each other, for a plurality of genetic tests performed in the past; and generating, by the processor, a learning model for outputting a prediction of the genetic mutation concerning the patient in a case where tumor site genome data obtained by reading the base sequence included in the specimen collected from the tumor site of the patient and the normal site genome data is input by setting the tumor site genome data and the normal site genome data as input and the genetic mutation as output.

* * * * *